(12) United States Patent
Shishido et al.

(10) Patent No.: US 6,387,688 B1
(45) Date of Patent: May 14, 2002

(54) DNA FRAGMENTS HAVING BASIDIOMYCETE-DERIVED PROMOTER ACTIVITY AND EXPRESSION OF FOREIGN GENES UNDER CONTROL OF THE PROMOTER ACTIVITY

(75) Inventors: Kazuo Shishido; Susumu Kajiwara, both of Kanagawa; Akira Tsukamoto, Tokyo, all of (JP)

(73) Assignee: Oji Paper Co., Ltd. (JP)

( * ) Notice: Subject to any disclaimer, the term of this patent is extended or adjusted under 35 U.S.C. 154(b) by 0 days.

(21) Appl. No.: 09/503,505

(22) Filed: Feb. 14, 2000

(30) Foreign Application Priority Data

Feb. 15, 1999 (JP) ............................. 11-036367
Mar. 31, 1999 (JP) ............................. 11-093777

(51) Int. Cl.$^7$ ............................. C12N 1/14; C12N 9/02; C12P 21/06; C07H 21/04
(52) U.S. Cl. ............................. 435/254.11; 435/69.1; 435/189; 536/23.1
(58) Field of Search ............................. 435/69.1, 189, 435/254.11; 536/23.1

(56) References Cited

U.S. PATENT DOCUMENTS 5,362,640 A * 11/1994 Tsukamoto et al. ....... 435/172.3
6,075,138 A * 6/2000 Kojima et al. ............. 536/24.1

FOREIGN PATENT DOCUMENTS

JP          09047289          2/1997

OTHER PUBLICATIONS

Kajiwara S. et al, Isolation and sequence of a developmentally regulated puttive novel gene, priA, form the basidiomycete *Lentinus edodes*, Gene (1992), 114: 173–178.*
Hori K. et al, Cloning, sequence analysis and transcriptional expression of a ras gene of the edible basidiomycete *Lentinus edodes*, Gene (1991), 105: 91–96.*

Ogawa K., Molecular breeding of the basidiomycete *Coprinus cinereus* strains with high lignin–decoloration and –degradation activities using novel heterologous protein expression vectors, Appl. Microbiol. Biotechnol. (1998) 49: 285–289.*
Takashi Yamazaki et al., "Structure and Function in *Escherichia coli* of Plasmids Containing Pyrimidine/Purine–Biased Stretch Originated from the 5'–Flanking Region of the Basiodiomycete ras Gene", *J. Biochem.* 122:696–702 (1997).
Olga V. Korolijova–Skorobogat'ko et al., "Purification and characterization of the constitutive form of laccase from the basidiomycete *Coriolu hirsutus* and effect of inducers on laccase synthesis," *Biotechnol. Appl. Biochem.* 28:47–54 (1998).
Yasushi Kojima et al., "Cloning, Sequence Analysis, and Expression of Ligninolytic Phenoloxidase Genes of the White–rot Basidiomycete *Coriolus hirsutus*," *The J. of Biol. Chem.* 265(25):15224–15230 (1990).
Seito et al., "Isolation of ras Gene from the Basidiomycete *Coriolus hirsutus* and Structural Comparison with Other Basidiomycete ras Genes", Japan Soc. Biosc. Biotech. & Agrochem., 73:214 (1999)—Japanese Abstract and English translation.

* cited by examiner

*Primary Examiner*—Ponnathapu Achutamurthy
*Assistant Examiner*—Malgorzata A. Walicka
(74) *Attorney, Agent, or Firm*—Finnegan, Henderson, Farabow, Garrett & Dunner, L.L.P.

(57) ABSTRACT

This invention relates to a Coriolus hirsutus host cell transformed with a vector containing a basidiomycete-derived promoter region selected from the group consisting of basidiomycete-derived ras and priA gene promoter regions. This invention is particularly characterized in that the basidiomycete-derived promoter region is a Lentinus edodes-derived ras or priA gene promoter region or a Coriolus hirsutus-derived ras gene promoter region. This host cell can be utilized for the high productivity of lignin degrading enzymes.

16 Claims, 8 Drawing Sheets

Ba: BamHI, HindIII. Sa: SalI, EV: EcoRV

SEQUENCE LISTING

<160> NUMBER OF SEQ ID NOS: 10

<210> SEQ ID NO 1
<211> LENGTH: 1362
<212> TYPE: DNA
<213> ORGANISM: Coriolus hirsutus

<400> SEQUENCE: 1

| | | | | | |
|---|---|---|---|---|---|
| ggatccgcta | taccgaaagg | ccgcgacgtc | ctacacatgt | cagtcaagag a | acatgatgg     60 |
| gcgtcatgtg | gacagccgag | ctgaggatgt | attgcgcgag | ggtgttcatc g | agctgcgcg    120 |
| tttccgagaa | ctgctgtaga | acggacgagg | agcttcgaga | ggggctgcga t | ggtgggaaa    180 |
| tatctttccg | gcggttttgg | aagggccatt | aagagcagag | agatgcccgt c | caggacagg    240 |
| gaaggtcggg | tgcggactgt | ggagcatccg | cctgcgatcc | tacatgagac c | ggggcgag     300 |
| acggacatct | gggaaaggaa | tgacatgcag | ggaccgtgag | aggatataca t | gaatggtgg    360 |
| tggtagacat | accacgatgc | tgggaacact | atccgtgatg | ttctcgcttg c | accagaaag    420 |
| gactgcaggt | ggggagcaat | cgcgccgaca | ggtggcgtgc | tatgcagaac c | gcggcagtc    480 |
| tcgacagcac | cttacctctt | ggacgtatca | ctcacagtcc | tctcggccct t | cagatccaa    540 |
| tcgatcccgt | agtaacgtgc | gtcatctagg | agtggaaggt | tggttgaccg a | cctgacaag    600 |
| acataaccgg | atgcccattc | ggaaggctcg | gggggccaag | cgacctccgt g | tatgatcgc    660 |
| atgctatagc | tcgacgtcgg | gccgatagcg | gcgcaaatca | gagcaccgaa t | gatgaagca    720 |
| tctgagggaa | gatcattgca | tgagccatcc | tgaacaggtt | cgcaacgcgt c | tgggaacga    780 |
| gatgccatgc | tgctacggtg | atcctgatga | agcacagccc | gagatgcttg g | tgctggacc    840 |
| ccattggaag | ctgctcgact | tccttgtatg | ataatcggtc | tacatttctc g | accacagtt    900 |
| gcgcatccgc | ggtcagctga | catcgaaggg | gagcagtagt | acagttggtg a | gctctcggg    960 |
| ccttcgcggc | gcattgccaa | agacaccacc | gaatattgcg | aggccttgcg c | agcgcgatg   1020 |
| tggctaaata | tgccagagca | gctgtataag | ggccctgtga | ctcaccatgc g | agaactgcg   1080 |
| atatgtggct | gtcagataat | gcgatatacg | agtcggagcg | gaggcggaac t | ggggctggt   1140 |
| agggactcta | cttattgcgg | taccggtcag | aggatggcag | cgttcagtga c | aagtcgcga   1200 |
| agcgccgggc | gcgagtattt | ggctatgttt | gcggcgcggt | gtgttccaat a | gagggcgct   1260 |
| tccacgtctt | aattccctg  | tcctcctcga | cggatcacct | ctcctccctc c | cattcccgc    1320 |
| ccttcaaata | ccccctcca  | cctcctcctc | cgccatacag | cc           |               1362 |

<210> SEQ ID NO 2
<211> LENGTH: 3497
<212> TYPE: DNA
<213> ORGANISM: Coriolus hirsutus
<220> FEATURE:
<221> NAME/KEY: exon
<222> LOCATION: (1363)..(1371)
<221> NAME/KEY: intron
<222> LOCATION: (1372)..(1425)
<221> NAME/KEY: exon
<222> LOCATION: (1426)..(1465)

```
<221> NAME/KEY: intron
<222> LOCATION: (1466)..(1517)
<221> NAME/KEY: exon
<222> LOCATION: (1518)..(1592)
<221> NAME/KEY: intron
<222> LOCATION: (1593)..(1717)
<221> NAME/KEY: exon
<222> LOCATION: (1718)..(1800)
<221> NAME/KEY: intron
<222> LOCATION: (1801)..(1861)
<221> NAME/KEY: exon
<222> LOCATION: (1862)..(2055)
<221> NAME/KEY: intron
<222> LOCATION: (2056)..(2113)
<221> NAME/KEY: exon
<222> LOCATION: (2114)..(2240)
<221> NAME/KEY: intron
<222> LOCATION: (2241)..(2296)
<221> NAME/KEY: exon
<222> LOCATION: (2297)..(2419)

<400> SEQUENCE: 2
ggatccgcta taccgaaagg ccgcgacgtc ctacacatgt cagtcaagag a acatgatgg      60
gcgtcatgtg gacagccgag ctgaggatgt attgcgcgag ggtgttcatc g agctgcgcg    120
tttccgagaa ctgctgtaga acggacgagg agcttcgaga ggggctgcga t ggtgggaaa    180
tatctttccg gcggttttgg aagggccatt aagagcagag agatgcccgt c caggacagg    240
gaaggtcggg tgcggactgt ggagcatccg cctgcgatcc tacatgagac c gggggcgag    300
acggacatct gggaaaggaa tgacatgcag ggaccgtgag aggatataca t gaatggtgg    360
tggtagacat accacgatgc tgggaacact atccgtgatg ttctcgcttg c accagaaag    420
gactgcaggt ggggagcaat cgcgccgaca gtgggcgtgc tatgcagaac c gcggcagtc    480
tcgacagcac cttacctctt ggacgtatca ctcacagtcc tctcggccct t cagatccaa    540
tcgatcccgt agtaacgtgc gtcatctagg agtggaaggt tggttgaccg a cctgacaag    600
acataaccgg atgcccattc ggaaggctcg gggggccaag cgacctccgt g tatgatcgc    660
atgctatagc tcgacgtcgg gccgatagcg gcgcaaatca gagcaccgaa t gatgaagca    720
tctgagggaa gatcattgca tgagccatcc tgaacaggtt cgcaacgcgt c tgggaacga    780
gatgccatgc tgctacggtg atcctgatga agcacagccc gagatgcttg g tgctggacc    840
ccattggaag ctgctcgact tccttgtatg ataatcggtc tacatttctc g accacagtt    900
gcgcatccgc ggtcagctga catcgaaggg gagcagtagt acagttggtg a gctctcggg    960
ccttcgcggc gcattgccaa agacaccacc gaatattgcg aggccttgcg c agcgcgatg   1020
tggctaaata tgccagagca gctgtataag ggccctgtga ctcaccatgc g agaactgcg   1080
atatgtggct gtcagataat gcgatatacg agtcggagcg gaggcggaac t ggggctggt   1140
agggactcta ttattgcgg taccggtcag aggatggcag cgttcagtga c aagtcgcga   1200
agcgccgggc gcgagtattt ggctatgttt gcggcgcggt gtgttccaat a gagggcgct   1260
tccacgtctt aattcccctg tcctcctcga cggatcacct ctcctccctc c cattcccgc   1320
ccttcaaata ccccctcca cctcctcctc cgccatacac ccatgtccag g gtgcgtaca   1380
ccgacacacg gcgctgtcag ctatcctgac gcctgcgcag tcccagttct t gcgcgagta   1440
caagcttgtc gtcgtcggcg gtggtggtca gttccccggc tcgctagcat c ccggactcg   1500
tctcacgcgt cctttcaggt gtcggcaagt ccgcactcac tatccagttc a ccagagtc   1560
acttcgtgga cgagtatgac cctaccatcg aaggtgtgta cctgttcctg a cgctctcgc   1620
ccacgtcgtc tcccgcttgc gaccatgccg catggccgag acgtcttgcg t tcccgcgaa   1680
```

-continued

```
gctttcccat ggtacgcgtg ctcacggcac ctcttacaga ctcgtaccgt a agcaatgcg      1740
tgattgacga tgaggtcgcg ctcctcgacg tcttggatac cgctggccag g aggaatacg     1800
ggtgcgtcta tcctctacac tccgtttttct cgcctctcac aacgtttgtt t gcgccgtgc    1860
agtgcgatgc gtgagcagta catgcgcacg ggggagggct tcctgctggt c tactccatc    1920
acttcgcgca actcgttcga ggaaatcagc acgttccatc agcagatcct a cgcgtaaag    1980
gaccaggact cgttcccggt catcgtcgtc gcaaacaagt gcgacttgga g tacgagcgg    2040
caggtgggaa tgaatggtac gttcacctcc ccacccttgc tcggtagact g cgtgtgctg    2100
actaagtgtg tgcgccgtgc agagggccgt gatctcgcga agcacttcgg c tgcaagttc    2160
atcgagactt cggcgaagaa ccgcatcaac gtcgacgagg cgttcagtca g ctcgtccgc    2220
gagatccgga agtacaacaa ggttcgttcg ccacaatttg ccgttaccac a ggctccagt    2280
acttacctct cccgcaggag caacaaaccg gacgtccggg cgtgcagccc a gcgcaccta    2340
gcgcccctgg cgtgtacggc aacgaaaagg acacccaga cgacggcgcg g gcggatgct    2400
gtggctgcgt tgtcgcgtaa ccgtcccatc cctcctccct tccttcatcg t ttctttttcc   2460
atcggtttgg gctcttcctg cgtacccgt tcttctcgtc ctgccacacc c tcatcgtcg    2520
ccattgcccg tcgtcactgc cagttctccc ccggatatca agatgtctct c atctcccgc    2580
tgctgttctg tttttatgta ttccttactc ttctgcgctc gtctgtccgt c tgaacatca    2640
tacctcgtgc ctagttcgcg ccgttggtgt gcgttctctg tttgtgactg t cggcattta    2700
ctgtccctac tcgttcgtcc cgattgattg ctgctgttca ttggattgac g gccgaatca    2760
aacatataga ggctttgagc cagagtcaaa ttatgatttg actagactag t gagaaagca    2820
gatttcgaca ccaccccgtt cgttgatcaa ggactgagta tggcgatacc t ggtatggat    2880
cagctcaagg attcttgtgc ttgttgtata cagcgccatg tcaagcactc a gtttgttct    2940
cgcacgtgcc ttggcctggg tcattccgag aatccatcca ctgtcgcagg a tctacgtct    3000
gccgccgcat gcatgccagt cccgaggcgg ctgaagtctg aggctctgag c agcccaact    3060
acagcctaac tgctggctag tacgtgagtc tgtcccaaga cattattcgc t ctattacag    3120
cacactgacc ttcgctttga acagctcctt gcgactatat aggcaccgat g tgcctccgc    3180
cacagagcac tacactcagg aagccacgct gtcaaggaat gcgcacatga t agtccgaga    3240
agcgcatggc gctacgcgga atgggcacca agtgtccgcg tcaggtttgg t ctggcattc    3300
ttctgatctt ccccgggct gaccgcaggt ggcccagatg cttgtttgtc g gcgctataa    3360
agtaggtgga cccgagtttc tcccagtctt tcgtaggtgg gcgactcgct a cacagtcag    3420
aagagtacga catcctatgt agggctacaa cgactgccaa acggaggct g taagtgagg    3480
ctcacggatt cggatcc                                                    3497
```

<210> SEQ ID NO 3
<211> LENGTH: 213
<212> TYPE: PRT
<213> ORGANISM: Coriolus hirsutus

<400> SEQUENCE: 3

Met Ser Arg Phe Leu Arg Glu Tyr Lys Leu Val Val Val Gly Gly Gly
1               5                   10                  15

Gly Val Gly Lys Ser Ala Leu Thr Ile Gln Phe Ile Gln Ser His Phe
            20                  25                  30

Val Asp Glu Tyr Asp Pro Thr Ile Glu Asp Ser Tyr Arg Lys Gln Cys
        35                  40                  45

```
Val Ile Asp Asp Glu Val Ala Leu Leu Asp V al Leu Asp Thr Ala Gly
    50                  55                  60

Gln Glu Glu Tyr Gly Ala Met Arg Glu Gln T yr Met Arg Thr Gly Glu
65                  70                  75                  80

Gly Phe Leu Leu Val Tyr Ser Ile Thr Ser A rg Asn Ser Phe Glu Glu
                85                  90                  95

Ile Ser Thr Phe His Gln Gln Ile Leu Arg V al Lys Asp Gln Asp Ser
                100                 105                 110

Phe Pro Val Ile Val Ala Asn Lys Cys A sp Leu Glu Tyr Glu Arg
            115                 120                 125

Gln Val Gly Met Asn Glu Gly Arg Asp Leu A la Lys His Phe Gly Cys
    130                 135                 140

Lys Phe Ile Glu Thr Ser Ala Lys Asn Arg I le Asn Val Asp Glu Ala
145                 150                 155                 160

Phe Ser Gln Leu Val Arg Glu Ile Arg Lys T yr Asn Lys Glu Gln Gln
                165                 170                 175

Thr Gly Arg Pro Gly Val Gln Pro Ser Ala P ro Ser Ala Pro Gly Val
                180                 185                 190

Tyr Gly Asn Glu Lys Gly His Pro Asp Asp G ly Ala Gly Gly Cys Cys
                195                 200                 205

Gly Cys Val Val Ala
        210

<210> SEQ ID NO 4
<211> LENGTH: 20
<212> TYPE: DNA
<213> ORGANISM: Artificial Sequence
<220> FEATURE:
<223> OTHER INFORMATION: Description of Artificial  Sequence: Designated
      is a probe for screening clones containing a ras gene from
      Coriolus hirsutus strain IFO4917.
<221> NAME/KEY: modified_base
<222> LOCATION: (9)
<223> OTHER INFORMATION: inosine

<400> SEQUENCE: 4
cayttygtng aygartayga                                                       20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial  Sequence: Designated
      is a sense primer for synthesizi ng a 1.4 kbp BamHI-NcoI fragment
      containing the ras gene promoter region from Coriolus hirsutus
      strain IFO4917 by PCR.

<400> SEQUENCE: 5
ggatcccgct ataccgaaag g                                                     21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial  Sequence: Designated
      is an antisense primer for synth esizing a 1.4 kbp BamHI-NcoI
      fragment containing the ras gene promoter region from Coriolus
      hirsutus strain IFO4917 by PCR.

<400> SEQUENCE: 6
ccatggctgt atggcggagg                                                       20
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial  Sequence: Designated
     is a sense primer for synthesizi ng a 2.2 kbp NcoI-EcoRI fragment
     containing manganese peroxidase struct ural gene region from
     Coriolus hirsutus strain IFO4917.

<400> SEQUENCE: 7
ccatggcttt caagacactc g                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial  Sequence: Designated
     is a sense primer for synthesizi ng a 2.2 kbp NcoI-EcoRI fragment
     containing manganese peroxidase struct ural gene region from
     Coriolus hirsutus strain IFO4917 by  PCR.

<400> SEQUENCE: 8
gaattcgcat gtaggtccgc g                                              21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial  Sequence: Designated
     is a sense primer for synthesizi ng a 2.4 kbp NcoI-EcoRI fragment
     containing laccase structural gene region from Coriolus hirsutus
     strain IFO4917 by PCR.

<400> SEQUENCE: 9
ctcgaggttc cagtctctg                                                 19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial  Sequence: Designated
     is a sense primer for synthesizi ng a 2.4 kbp NcoI-EcoRI fragment
     containing laccase structural gene region from Coriolus hirsutus
     strain IFO4917 by PCR.

<400> SEQUENCE: 10
gaattcccgg ggacgtatac g                                              21

US 6,387,688 B1

DNA FRAGMENTS HAVING BASIDIOMYCETE-DERIVED PROMOTER ACTIVITY AND EXPRESSION OF FOREIGN GENES UNDER CONTROL OF THE PROMOTER ACTIVITY

BACKGROUND OF THE INVENTION

1. Field of the Invention

This invention relates to use of DNA fragments having promoter activity from basidiomycetes, particularly Coriolus hirsutus and Lentinus edodes in production of useful polypeptides such as lignin degrading enzymes. More specifically, this invention relates to a Coriolus hirsutus host cell transformed with a vector including a Coriolus hirsutus-derived ras promoter region or a Lentinus edodes-derived ras or priA promoter region, and to a method for producing useful polypeptides using the host cell.

According to this invention, polypeptides such as lignin degrading enzymes, the production of which has been considered to be difficult, can be supplied stably and in large quantity by genetic recombination technique using the host-vector system, particularly basidiomycete-derived host-vector system, of the present invention.

2. Background Art

Conventionally, wood pulps have been produced popularly by methods of chemically treating woods. However, from the viewpoint of environmental problems or the like, there has been an attempt to produce a cellulose pulp by inoculating a white rotting fungus into a lignocellulose substance of wood or the like then culturing the fungus to degrade lignin (Japanese Patent Application Laid-open No. 46,903/1975). However, the white rotting fungus used in this method has problems that the coexisting carbohydrates are degraded or, in cases of using cellulase-deficient mutants, their native lignin degrading ability becomes weaken, so that this method has not yet been put into practice.

In order to solve such problems as above, there has been an attempt to make a lignin degrading enzyme from a white rotting fungus act on a lignocellulose substance to selectively degrade lignin alone (Science, 221, 661 (1983)). This report, though mainly a lignin model compound is used as a substrate, is the first one in the world in which a lignin degrading enzyme was isolated and purified. This enzyme is an extracellular enzyme which Phanerochaete chrysosporium produces, and the main characteristics of the enzyme are as follows: the optimum pH is 3.0; it is an iron-containing enzyme; the molecular weight is 41,000 to 42,000 Da; hydrogen peroxide is necessary for enzymatic reaction; and it is confirmed to act on a compound formed by replacing the phenolic hydroxyl group at position 4 of a lignin model compound with a methoxyl group. This enzyme is lignin peroxidase, and the existence of plural isozymes are known (FEBS Lett., 169, 247 (1984)). Lignin peroxidase is found from many wood-rotting fungi such as Coriolus versicolor, Bjerkandera adusta, etc. other than the above, some of which have been purified.

On the other hand, lignin degrading enzymes to be produced by Coriolus hirsutus and Lenzites betulina are also known (Japanese Patent Application Laid-open Nos. 220, 190/1987 and 220,189/1987), which are phenol oxidases, and their main characteristics are that the optimum pH is 4.5, that they are copper-containing enzymes, that the molecular weight is approximately 63,000 Da or approximately 65,000 Da, that the isoelectric point is around 3.5, that oxygen is necessary for the enzymatic action, and that they do not act on a compound formed by replacing the phenolic hydroxyl group at position 4 of a lignin model compound with a methoxyl group but on a phenolic lignin model.

Besides, manganese peroxidase is one of typical lignin degrading enzymes, the main characteristics of which are that the molecular weight is 46,000 Da or less, that it is presumed to be an iron-containing enzyme, that hydrogen peroxide is necessary for the enzymatic action, that the enzyme reaction is Mn(II)-dependent, that it is confirmed to never act on a compound formed by replacing the phenolic hydroxyl group at position 4 of a lignin model compound with a methoxyl group but on a phenolic lignin model, and therefore it is an enzyme having properties quite different from those of the lignin peroxidase.

Up to now, the production of varieties of polypeptides by recombinant DNA techniques has been carried out using a host system centering around Escherichia coli (also designated E. coli). However, there are many cases where E. coli is not appropriate as a host. For example, there are many problems, in cases of producing useful polypeptides (e.g., enzymes) from a higher animal such as human being or the like, that the polypeptide of interest is not produced as an active protein, and that a large number of toxic substances other than the polypeptide of interest are produced making the purification of the target product very difficult. As alternative means for solving these problems, production methods using yeast, a lower eukaryote, as a host have been studied extensively, which however newly bring about a problem of low productivity. For the purpose of polypeptide production, transformation systems using higher eukaryotes such as filamentaous fungi (e.g. Aspergillus) and basidiomycetes (e.g. Phanerochaete and Coriolus) as hosts have also been developed, and the production of lignin degrading enzymes using the system has been studied.

Basidiomycetes belong to eukaryotes and are considered more closely related to animal cells than yeast (T. L. Smith, Proc. Natl. Acad. Sci. USA, 86, 7063 (1989)). Coriolus hirsutus having a strong lignin degrading ability is a basidiomycete belonging to the genus Coriolus, whose host-vector system has been developed by the present inventors employing recombinant DNA techniques. As a result, the present inventors succeeded in the production of lignin peroxidase that had been considered to be difficult so far (Japanese Patent Application Laid-open No. 054,691/1994). However, the promoter region used therein was a promoter region of the ornithine carbamoyltransferase gene (hereinafter referred to as "OCT gene"), which is a gene for amino acid synthetase, or a promoter region of the phenol oxidase gene participating in lignin degradation, so there were problems that the productivity of the lignin peroxide was as low as that produced by a wild strain IFO4917 cultured in a lignin peroxidase production medium (low carbon and nitrogen sources), and that it took a lot of time for gene expression because the target enzyme was obtained as a secondary metabolite. In addition, it has been reported that a promoter, which is provided for enzyme protein production systems by genetic recombination of other organism species (e.g. filamentous fungi), was not function in basidiomycetes (A. Lorna et. al., Curr. Genet., 16, 35 (1989)). Furthermore, ArgB gene from Aspergillus nidulans did not function in Coriolus hirsutus (A. Tsukamoto et al., U.S. Pat. No. 5,362, 640).

Therefore, the present inventors obtained a promoter for constitutively expressing Coriolus hirsutus glyceraldehyde-3-phosphate dehydrogenase (GPD) gene, ligated thereto a structural gene with signal peptide coding sequence of a high temperature-induced lignin peroxidase gene (Japanese Patent Application Laid-open No. 260,978/1993) or a manganese per-oxidase gene (Japanese Patent Application Laid-open No. 308,581/1996) cloned from the Coriolus hirsutus, transformed the ligated product into an ornithine carbamoyltransferase-deficient Coriolus hirsutus mutant, and thereby succeeding in obtaining a strain capable of highly producing lignin peroxidase or manganese peroxidase (Japanese Patent Application Laid-open No. 47,289/1997).

However, in spite of the above technical proposal, a growing interest is taken in a promoter having a strong transcription activity and enabling high expression of a useful polypeptide.

Under such circumstances, the present inventors noticed a basidiomycete host-vector system and searched for various promoters functioning in this system.

Therefore, an object of the present invention is to provide a promoter for allowing a host such as basidiomycete or to produce a useful polypeptide in a large quantity.

Another object of the present invention is to provide a host-vector system including the promoter and a hyperexpression and production method of a useful polypeptide utilizing the system.

SUMMARY OF THE INVENTION

The present inventors noticed a constitutively expressing Coriolus hirsutus ras gene and Lentinus edodes ras and priA genes, the priA gene being expresses highly when a fruit body primoridium is formed in Lentinus edodes, cloned a DNA fragment encoding the ras gene or the priA gene from a Coriolus hirsutus or Lentinus edodes chromosomal DNA restriction fraction, sequenced a promoter region upstream of this gene, and found for the first time that this promoter region was effective for the expression of a gene encoding a useful polypeptide in a hostvector system, particularly Coriolus hirsutus host-vector system. Furthermore, the present inventors ligated a structural gene with signal peptide coding sequence of a manganese peroxidase gene, high temperature-induced lignin peroxidase gene (Japanese Patent Application Laid-open No. 260,978/1993), or laccase gene, the structural gene having been cloned from Coriolus hirsutus, to a site downstream of the above promoter region, introduced the same into an OCT-deficient Coriolus hirsutus mutant, and thereby succeeded in obtaining a manganese peroxidase-, lignin peroxidase- or laccase-highly producing strain with an ability to strongly degrade lignin.

That is, the present invention is summarized as follows.

(1) A Coriolus hirsutus host cell transformed with a vector containing a basidiomycete-derived promoter region selected from the group consisting of ras and priA gene promoter regions from basidiomycetes.

(2) A host cell defined in (1) above, wherein the ras gene promoter region is derived from Coriolus hirsutus or Lentinus edodes.

(3) A Coriolus hirsutus host cell defined in (1) above, wherein the priA gene promoter region is derived from Lentinus edodes.

(4) A Coriolus hirsutus host cell defined in (1) above, wherein the vector further comprises a gene encoding a useful polypeptide, the gene being transcribably ligated to a site downstream of the foregoing promoter region.

(5) A Coriolus hirsutus host cell defined in above (3), wherein the said gene encoding a useful polypeptide is a gene coding for a lignin degrading enzyme such as manganese peroxidase, lignin peroxidase, or laccase.

(6) A process for producing a useful polypeptide comprising culturing the Coriolus hirsutus host cell recited in (1) above in a medium and recovering the formed useful polypeptide.

(7) A process defined in (6) above, wherein the useful polypeptide is a lignin degrading enzyme such as manganese peroxidase, lignin peroxidase, or laccase.

(8) An isolated DNA fragment containing a Coriolus hirsutus-derived ras gene promoter region.

(9) An isolated DNA fragment defined in (8) above, wherein the DNA fragment has a nucleotide sequence shown in SEQ ID NO:1 or a sequence that hybridizes to a sequence complementary to the nucleotide sequence under stringent conditions and has a promoter activity.

(10) A recombinant DNA, which contains a gene encoding a useful polypeptide and the DNA fragment recited in (8) above, the said gene being transcribably linked to the DNA fragment.

(11) A recombinant DNA defined in (10) above, wherein the gene encoding a useful polypeptide is a gene coding for a lignin degrading enzyme such as manganese peroxidase, lignin per-oxidase, or laccase.

(12) A DNA containing a Coriolus hirsutus-derived ras gene promoter sequence and ras gene sequence and has a nucleotide sequence shown in SEQ ID NO:2.

(13) A vector containing the DNA fragment recited in (8) above or the recombinant DNA in (10) above.

(14) A host cell transformed with the vector recited in (13) above.

(15) A host cell defined in (14) above, wherein the host is a basidiomycete.

(16) A host cell defined in (15) above, wherein the basidiomycete is Coriolus hirsutus

(17) A process for producing a useful polypeptide, comprising culturing the host cell recited in (13) above in a medium and recovering the formed useful polypeptide.

(18) A process defined in (17) above, wherein the useful polypeptide is a lignin degrading enzyme such as manganese peroxidase, lignin peroxidase, or laccase.

DETAILED DESCRIPTION OF THE INVENTION

Hereinafter the present invention will be described in detail.

In the first aspect, the present invention provides a DNA fragment containing a Coriolus hirsutus-derived ras promoter sequence.

The DNA fragment according to the present invention can be obtained through the following procedures.

Chromosomal DNA is prepared according to an ordinary chromosomal DNA extraction technique such as the method of Yelton et al. (Proc. Natl. Acad. Sci. USA, 81, 1470 (1984)) from Coriolus hirsutus (e.g., IFO4917 strain), and the obtained chromosomal DNA is treated with at least one appropriate restriction enzyme such as Sau3AI so as to partially degrade the DNA and then fractionated by sucrose gradient ultracentrifugation to obtain 10-kbp to 25-kbp DNA fragments. The DNA fragments obtained above are inserted into phage DNA treated with a restriction enzyme enabling the formation of the same cohesive end, thereby to generate a chromosomal gene library. As the phage DNA, EMBL3 (A–M, Frishauf et al., J. Mol. Biol. , 170, 827 (1983)) or λ phage DNA can be used. After insertion, packaging is carried out in vitro to give a chromosomal gene library. For subcloning, a plasmid such as pUC18 (C. Yanisch-Perron et al., Gene, 33, 103 (1985)) can be used. A cloning vector is not limited to those exemplified above, and commercially available ones or ones described in literature can also be used as the cloning vector. Next, from the obtained chromosomal gene library, a clone containing both a ras gene and a ras promoter region is selected by plaque hybridization using a synthetic DNA probe made on the basis of a nucleotide sequence of a ras gene isolated from other organism species. From the selected clone, a DNA fragment containing the target gene is isolated, of which a restriction map is made and a sequence is determined.

The sequencing can be carried out by inserting the above fragment containing ras chromosomal gene into an appropriate cloning vector (e.g., a pUC vector such as pUC19) and then following the method of Sanger et al. (Proc. Natl. Acad. Sci. USA, 74, 5463 (1977)).

Figure 5:
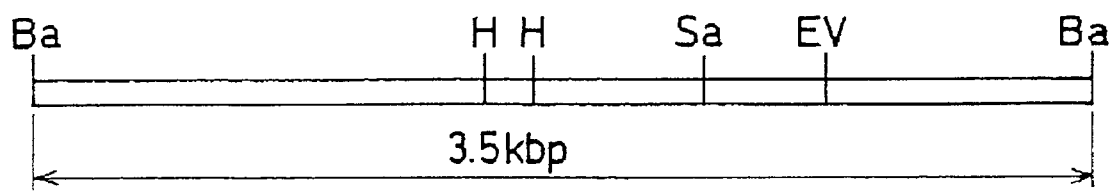
FIG. 5 shows a chromosomal restriction map of a region containing Coriolus hirsutus-derived ras gene and promoter region thereof.

According to the above procedures, the restriction map shown in FIG. 5 and the nucleotide sequence shown in SEQ ID NO:2 were determined. A gene carrying this sequence is a 3497 bp genomic gene containing a Coriolus hirsutus-derived ras gene and a ras gene promoter region upstream of the ras gene. In this sequence, the promoter region exists between nucleotide Nos. 1–1362 (SEQ ID NO:1), and TATAA at nucleotide Nos. 1045–1049 and CCAAA at nucleotide Nos. 977–981 are recognized respectively. On the other hand, the ras gene exists between Nucleotide Nos. 1363–2419 and is composed of 7 exons and 6 introns (intervening sequences). Specifically, the exons and introns exist as follows respectively; Exon 1 exists between 1363–1371, Intron 1 between 1372–1425, Exon 2 between 1426–1465, Intron 2 between 1466–1517, Exon 3 between 1518–1592, Intron 3 between 1593–1717, Exon 4 between 1718–1800, Intron 4 between 1801–1861, Exon 5 between 1862–2055, Intron 5 between 2056–2113, Exon 6 2114–2240, Intron 6 between 2241–2296, and Exon 7 between 2297–2419. Besides, the region between nucleotide Nos. 2420–3497 is a 3' non-translational region containing a terminator. From the sequence analysis, Coriolus hirsutus ras protein was found to have the amino acid sequence given in SEQ ID NO:3 with 213 amino acids.

Escherichia coli strain DH5α/pCHRAS carrying a genomic gene fragment containing Coriolus hirsutus-derived ras gene/promoter sequence (SEQ ID NO:2) was deposited in National Institute of Bioscience & Human-Technology, Agency of Industrial Science & Technology (Higashi 1-1-3, Tsukuba-shi, Ibaraki-ken, 305–8566 Japan) on Mar. 30, 1999and was given the Accession No. FERM P-17352, which deposit was transferred to the international deposit on Jan. 20, 2000 in accordance with the terms of the Budapest Treaty and given the Accession No. FERM BP-7001. The DNA having the nucleotide sequence shown in SEQ ID NO:2 contained in this deposited strain is included within the scope of the present invention.

A DNA fragment containing the ras gene promoter region can be obtained from the above fragment containing ras chromosomal gene by PCR (polymerase chain reaction). As primers for PCR, sequences with approximately 10 to 50 nucleotides, preferably approximately 15 to 30 nucleotides based on the nucleotide sequence shown in SEQ ID NO:1 and their complementary sequences can be used as sense and antisense primers. For example, the sense and antisense primers shown in SEQ ID NOS:5 and 6, respectively, can be used (see Example 11 below).

As used herein, the term "Promoter sequence" or "promoter region" refers to a sequence or region having a function to regulate the transcription of a structural gene, and it at least contains a functional nucleotide sequence motif that is substantially conserved in eukaryotic promoters (e.g., TATA, CCAA, and GC boxes). Therefore, the nucleotide sequence given in SEQ ID NO:1 is an specific example of such promoter sequences, and a sequence hybridizing to a sequence complementary to the said nucleotide sequence under stringent conditions or a sequence containing mutation or modification such as deletion, substitution or addition of one or more nucleotides in the said nucleotide sequence also falls in the scope of the present invention. Such mutation or modification can be conducted by employing a well-known site-specific mutagenesis technique such as oligonucleotide site-specific mutagenesis, or cassette mutagenesis, based on the nucleotide sequence given in SEQ ID NO:1 (e.g., see Short Protocols In Molecular Biology, Third Edition, John Wiley & Sons, Inc.).

As used herein, the term "Stringent Conditions" means conditions where it is possible to hybridize to a mutated or modified sequence having 70% or higher, preferably 80% or higher, more preferably 90% or higher, particularly 95% or higher homology to the complementary strand of the nucleotide sequence shown in SEQ ID NO:1. Generally, hybridization conditions are determined in consideration of factors such as temperature, ion intensity and the like, and it is known that stringency generally becomes higher as the temperature becomes higher and/or as the ion intensity becomes lower. Specific conditions are an ion intensity of 6×SSC and a hybridization temperature of 68° C.

In the second aspect, the present invention provides a recombinant DNA which contains both a gene encoding a useful polypeptide and a DNA fragment containing Coriolus hirsutus-derived ras gene promoter sequence, the said gene being transcribably linked to the said DNA fragment.

As used herein, the term "transcribably" means that the transcription of the above gene into mRNA takes place under the action of a promoter in a host. A gene encoding a useful polypeptide is linked at a site downstream of a DNA fragment containing a promoter sequence and transcribed into mRNA by action of the promoter. As a gene encoding a useful polypeptide, any non-limited gene can be used. Examples thereof include genes for lignin degrading enzymes such as manganese peroxidase, lignin peroxidase, laccase, etc. These genes are obtainable according to the well-known genome or cDNA cloning techniques and PCR techniques using sequences registered in gene banks or sequences described in literature. Alternatively, in cases of deposited genes, genes available by request for furnished samples can be used. The DNA fragment containing a promoter sequence and the gene encoding a useful polypeptide can be ligated together using an appropriate DNA ligase after, optionally, introducing a restriction site and making blunt-ends or cohesive ends. As recombinant DNA techniques including cloning, ligation, PCR, etc., those described, for example, in J. Sambrook et al., Molecular Cloning, A Laboratory Manual, Second Edition, Cold Spring Harbor Laboratory press, 1989 and Short Protocols In Molecular Biology, Third Edition, A Compendium of Methods from Current Protocols in Molecular Biology, John Wiley & Sons, Inc. can be used.

In the third aspect, the present invention provides a vector containing the DNA fragment or recombinant DNA defined above.

A vector, but not limited to a specific type of vector, is selected depending on the kind of a host to be transformed with the vector. Used as the vectors are ones autonomously replicable in a prokaryotic or eukaryotic host cell or ones homologously integrated in the chromosome, including plasmids, viruses, phages, cosmids, etc. The vector can optionally include a selective marker, an origin of replication, a terminator, a polylinker, an enhancer, a ribosome binding site, etc. Since various vectors for prokaryotes and eukaryotes such as bacteria, fungi, yeasts, animals and plants are commercially available or are described in literature, the DNA fragment or recombinant DNA of the invention can be inserted into the aforementioned vectors. The insertion of the DNA can be carried out by utilizing known techniques such as those described in J. Sambrook et al. (ibid).

In the fourth aspect, the present invention further provides a host cell transformed with the vector prescribed above.

Here, any host cell can be selected from fungi including basidiomycetes, filamentous fungi, and yeasts, other eukaryotic cells (e.g., animal cells, plant cells, insect cells and algae) and prokaryotic cells (e.g., bacteria and blue-green algae) as far as a structural gene of interest is expressed under the control of the promoter. A preferable host cell is Coriolus hirsutus, which is a class of basidiomycetes. Methods of transformation include, but are not limited to, calcium chloride/PEG method, calcium phosphate method, lithium acetate method, electroporation method, protoplast method, spheroplast method, lipofection method, and agrobacterium method. In examples described later, an expression example using Coriolus hirsutus as a host is given, in which the ornithine carbamoyltransferase (OCT)-deficient Coriolus hirsutus auxotrophic mutant OJI-1078 (Accession No. FERM BP-4210) is used as a host.

In the fifth aspect, the present invention provides a process for producing a useful polypeptide comprising culturing the above transformed host cell in a medium and recovering the produced useful polypeptide.

A polypeptide is produced in a secretory form when it is expressed and translated in a fusion form with a signal peptide, and in this case the polypeptide can directly be isolated from a medium. On the other hand, when a polypeptide is produced in a non-secretory form, cells are isolated and then destroyed by treatments such as ultrasonication or homogenization to obtain an extract, from which the polypeptide can be isolated. Isolation and purification can be carried out by adopting methods such as solvent extraction, salting out, desalting, organic solvent precipitation, ultrafiltration, ion exchange, hydrophobic interaction, HPLC, gel filtration, affinity chromatography, electrophoresis, chromatofocusing, etc., which are used alone or in combination.

For example, when the structural gene portion for manganese peroxidase, lignin peroxidase or laccase is ligated at a site downstream of the promoter region of the invention and recombinant DNA techniques are employed, the manganese peroxidase, lignin peroxidase or laccase can be produced in a large quantity. An Escherichia coli recombinant strain JM109/pBSMPOC1 containing a Coriolus hirsutus-derived manganese peroxidase cDNA (Japanese Patent Application Laid-Open No. 308581/1996), an Escherichia coli recombinant strain JM109/pBSMPOG1 containing a manganese peroxidase chromosomal gene (Japanese Patent Application Laid-Open No. 308581/1996), an Escherichia coli recombinant strain E. coli XL-1 blue/pBSLPOG7 containing a high temperature-induced lignin peroxidase gene (Japanese Patent Application Laid-Open No. 260978/1993), and an Escherichia coli recombinant strain containing a laccase (also named phenol oxidase) gene (Japanese Patent Publication Nos. 46,995/1995 and 85,717/1994) have been deposited in the National Institute of Bioscience & Human-Technology, Agency of Industrial Science & Technology (Higashi 1-1-3, Tsukuba-shi, Ibaraki-ken, Japan) under Accession Nos. FERM P-14932, FERM P-14933, FERM P-12683, and FERM BP-2793 (chromosomal gene), FERM P-10055 (cDNA) or FERM P-10061 (cDNA), respectively.

In the sixth aspect, the present invention provides a Coriolus hirsutus host cell transformed with a vector containing a basidiomycete-derived promoter region selected from the group consisting of basidiomycete-derived ras gene promoter and priA gene promoter regions.

In one embodiment of the present invention, the ras gene promoter is derived from Lentinus edodes or Coriolus hirsutus, and the priA gene promoter from Lentinus edodes. Coriolus hirsutus ras gene promoter region can be obtained as above. Besides, the Lentinus edodes-derived ras gene promoter and priA gene promoter regions can be obtained from Lentinus edodes (e.g., MAFF-430002 available from Bio-Related Industrial Technology and Research Advancing Organization (http://www.brain.go.jp); MAFF-430002 strain) in accordance with the method described in FEMS Microbiology Letters, 92, 147 (1992) and Gene, 114, 173 (1992), respectively.

In the present invention, when a gene encoding a useful polypeptide is transcribably linked at a site downstream of the above promoter region in the above-described vector, a Coriolus hirsutus transformant obtained by transformation with the vector can produce the polypeptide in a high yield by culturing the transformant in an appropriate medium. Examples of such useful polypeptides include lignin degrading enzymes such as manganese peroxidase, lignin peroxidase and laccase.

As described above, basidiomycetes producing lignin degrading enzymes such as manganese peroxidase, lignin per- oxidase and laccase, particularly including a Coriolus hirsutus transformant ving an ability to highly degrade lignin, are provided according to the present invention. The transformant of the present invention has a property of acting on lignin so as to degrade it into low-molecular-weight products, so it can be applied to various steps in paper and pulp production processes using a lignocellulose material of wood or the like as a raw material. Besides, in saccarification of wood, this transformant can also be applied to the field of a so-called cellulose biomass utilization for increasing the cellulase action by decomposing lignin as a treatment at the preceding stage of saccarification.

EXAMPLES

Hereinafter, the present invention will be described in further detail with examples. However, the scope of the pre-sent invention is not limited by the examples.

Figure 1:
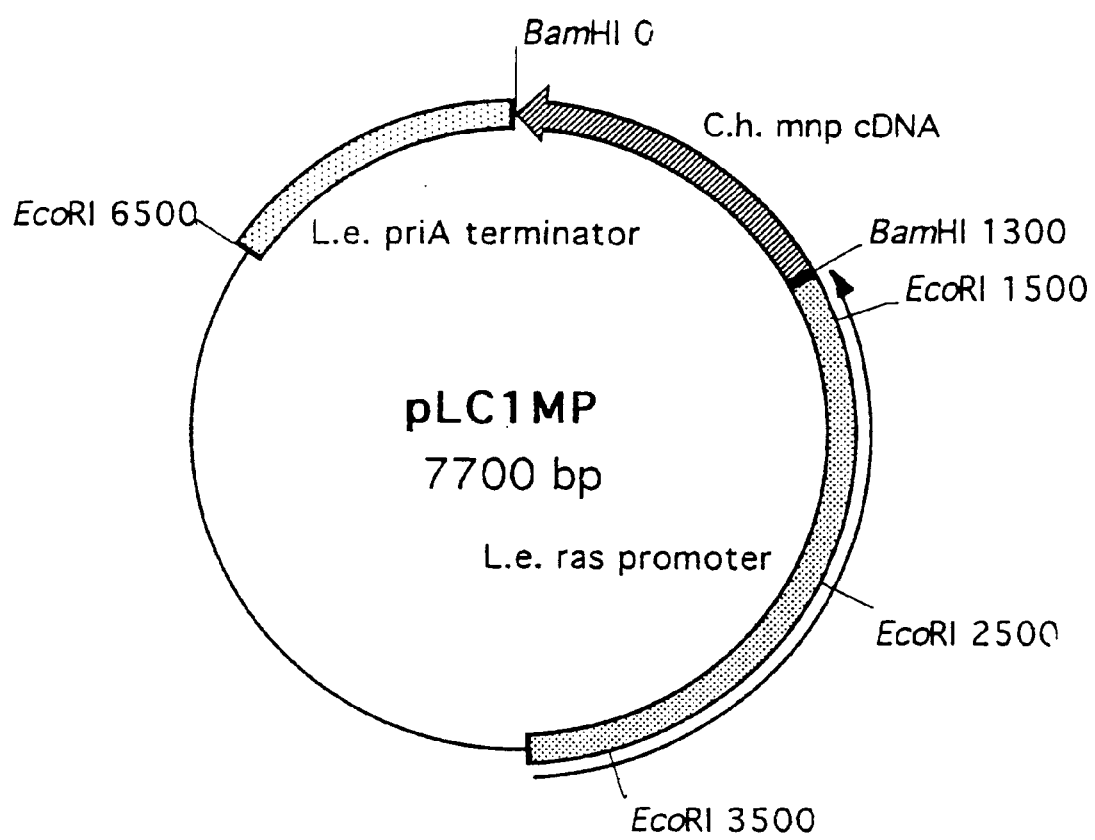
FIG. 1 shows a plasmid pLC1MP containing a Coriolus hirsutus-derived manganese peroxidase gene whose expression regulation is governed by a Lentinus edodes ras gene promoter region.

Example 1
Construction of Expression Vector Containing Coriolus hirsutus-Derived Manganese Peroxidase Gene with Lentinus edodes-Derived ras Gene Promoter A plasmid pLC1 (6.4 kb) containing a Lentinus edodes-derived ras gene promoter region (2.5 kb) and a priA gene terminator region (1.2 kb) (K. Ogawa et al., Appl. Microbiol. Biotechnol. (1998) 49, 285–289) was digested with a restriction enzyme BamHI (Takara Shuzo Co., Ltd., Kyoto, Japan), followed by ligating a Coriolus hirsutus-derived manganese peroxidase cDNA to the BamHI site in the forward direction to prepare a manganese peroxidase gene expression vector, which was designated as pLC1MP (FIG. 1).

Figure 2:
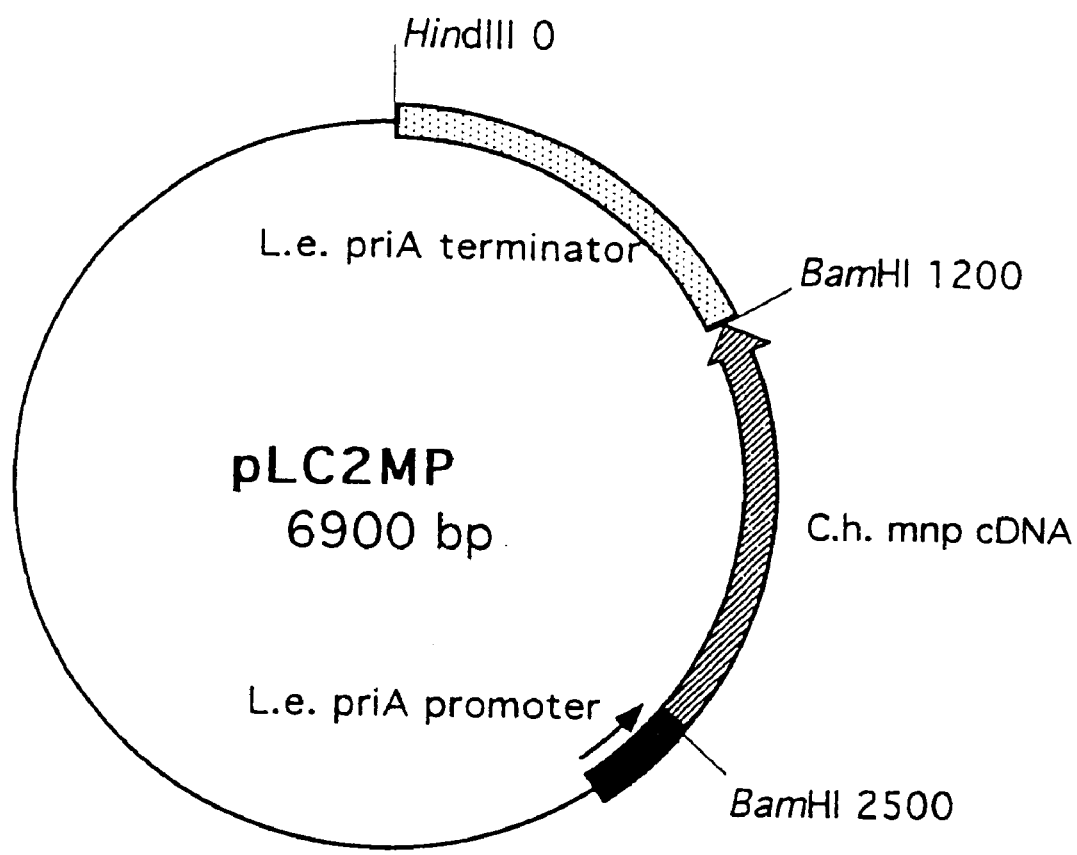
FIG. 2 shows a plasmid pLC2MP containing a Coriolus hirsutus-derived manganese peroxidase gene whose expression regulation is governed by a Lentinus edodes priA gene promoter region.

Example 2
Construction of Expression Vector Containing Coriolus hirsutus-Derived Manganese Peroxidase Gene with Lentinus edodes-Derived priA Gene Promoter A plasmid pLC2 (5.6 kb) containing a Lentinus edodes-derived priA gene promoter region (0.4 kb) and a priA gene terminator region (1.2 kb) (K. Ogawa et al., ibid) was digested with a restriction enzyme BamHI (Takara Shuzo Co., Ltd., Kyoto, Japan), followed by ligating a Coriolus hirsutus-derived manganese peroxidase cDNA gene to the BamHI site in the forward direction to prepare a manganese peroxidase gene expression vector, which was designated as pLC2MP (FIG. 2).

Example 3
Method for Transforming Coriolus hirsutus

The following procedures (a) to (c) were carried out, and a transformant was obtained by the following (d) and (e).

(a) Mononuclear hypha culture 100 ml of SMY medium (1% sucrose, 1% malt extract, 0.4% yeast extract) was dispensed in a 500-mL conical flask, in which approximately 30 glass beads (around 6 mm diameter) were placed, and sterilized. Then, agar piece (5 mm diameter) was punched out from a plate agar culture of Coriolus hirsutus strain OJI-1078 using a cork borer, which was then inoculated into a SMY medium and stationarily cultured at 28° C. for 7 days (preculture).

To fractionize the hypha, the medium was shaken once or twice a day. Next, 200 ml of the SMY medium was dispensed into a 1-L conical flask, in which a rotator was placed. After sterilization, the precultured hypha was filtered and collected with a nylon mesh (pore size, 30 μm) and stationarily cultured at 28° C. In this step, the hypha was fractionized by stirring with a stirrer for 2 hours a day. This culture was carried out for 4 days.

(b) Preparation of protoplast

The above liquid-cultured hypha was filtered and collected with a nylon mesh (pore size, 30 μm), followed by washing with an osmotic pressure regulating solution (0.5 M $MgSO_4$, 50 mM maleate buffer (pH5.6)). Next, the wet hypha (100 mg/ml) was suspended in a cell wall lysing enzyme solution and incubated at 28° C. for 4 hours with gently shaking to make protoplasts free. As the cell wall digesting enzyme, the following commercially available enzyme preparations were used in combination. That is, 5 mg of cellulase Onozuka RS (Yakult Co., Ltd.,Tokyo, Japan) and 10 mg of Yatalase (Takara Shuzo, Co., Ltd., Kyoto, Japan) were dissolved in 1 ml of the above osmotic pressure regulating solution, which was used as an enzyme solution.

(c) Purification of protoplast

After removing the fractionized hypha from the above enzymatic reaction mixture with a nylon mesh (pore size, 30 μm), the fractionized hypha and protoplasts remaining on the nylon mesh were washed once with the above osmotic pressure regulating solution in order to increase the recovery of protoplast. The obtained protoplast suspension was centrifuged (1,000×g, 5 minutes), followed by removing the supernatant. After resuspending the precipitate in 4 ml of 1 M sucrose solution (20 mM MOPS buffer (pH 6.4)), centrifugation was repeated and the resulting precipitate was washed twice with the above 1 M sucrose solution. Thus treated precipitate was suspended in 500 μl of a solution prepared by adding 40 mM calcium chloride to 1 M sorbitol solution (20 mM MES (pH 6.4)) to prepare a protoplast suspension, which was preserved at 4° C.

The protoplast concentration was determined by direct microscopic observation using a hemocytometer. The centrifugation steps were all carried out using a swing rotor at 1,000×g at room temperature for 5 minutes.

(d) Transformation-1

To 100 μl of the protoplast suspension with a concentration of $10^6$ cells/100 μl, 10 μg of plasmid pLC1MP prepared in Example 1 and 1 μg of pUCR1 containing an ornithine carbamoyltransferase chromosomal gene were added at the same time, followed by ice-cooling the mixture for 30 minutes. Then, an equal volume of a PEG solution (50% PEG3400, 20 mM MES (pH 6.4)) was added to the protoplast suspension, followed by ice-cooling for 30 minutes. Next, the ice-cooled mixture was mixed in a mini- mum soft agar medium (1% agar) containing 0.5 M sucrose and leucine and inoculated onto a plate. The plate was cultured at 28° C. for 4 days, whereby a transformant was obtained.

(e) Transformation-2

To 100 μl of the protoplast suspension with a concentration of $10^6$ cells/100 μl, 10 μg of plasmid pLC2MP prepared in Example 2 and 1 μg of pUCR1 containing an ornithine carbamoyltransferase chromosomal gene were added at the same time, followed by ice-cooling the mixture for 30 minutes. Then, an equal volume of a PEG solution (50% PEG3400, 20 mM MES (pH 6.4)) was added to the protoplastsuspension, followed by ice-cooling for 30 minutes. Next, the ice-cooled mixture was mixed with a mini-mum soft agar medium (1% agar) containing 0.5 M sucrose and leucine and inoculated onto a plate. The plate was cultured at 28° C. for 4 days, whereby a transformant was obtained.

Example 4
Decloration and Decomposition of Lignin with Transformant

The transformant obtained in Example 3 was inoculated in 10 ml of MYG medium (1% malt extract, 0.4% yeast extract, 0.4% glucose; pH 5.6) containing 10 mg of lignin (Tokyo Kasei Kogyo K. K., Tokyo, Japan) and 2.5 mg of $MnCl_2$ and subjected to shake culture at 30° C. Separately, a host strain OJI-1078 was inoculated into the same medium and similarly subjected to shake culture as a control. The degradation of lignin was measured serving as an indication the decrease in absorbance at 275 nm indicating cleavage of aromatic rings. The decoloration of lignin was measured serving as an indication the decrease in absorbance at 480 nm. As the result, the absorbance of 10 ml of MYG liquid medium containing 10 mg of lignin was 27.15 at 275 nm and 2.19 at 480 nm. These values at the start of culture were defined as 100%.

As the result, in the case of the transformant for manganese peroxidase expression using the ras gene promoter region, the degradation of lignin and decoloration was increased about 3 times as compared with the host as a control 16 days after the start of culture.

The transformant for manganese peroxidase expression using the priA gene promoter region showed about 4 times higher lignin degradation and decoloration than the case of only the host 12 days after the start of culture.

Example 5
Production of Manganese Peroxidase by Transformant

Five 50-mm$^2$ agar pieces containing each of the transformed strains obtained in Example 3 above were inoculated into 50 ml of glucose-peptone liquid medium (20 g/l glucose, 5 g/l peptone, 2 g/l yeast extract, 0.5 g/l KH$_2$PO$_4$·7H$_2$O, 48 mg/l MnSO$_4$·5H$_2$O; adjusted to pH 5.0 with phosphoric acid) in a 500-mL conical flask and cultured at 28° C. for 6 days with shaking. After 6 days, the obtained culture was centrifuged to obtain the supernatant.

The enzyme activity was measured by thoroughly mixing 50 μl of 0.5 M sodium malonate buffer (pH 5.5), 345 μl of enzyme solution, 5 μl of 10 mM hydrogen peroxide and 100 μl of 1 mM MnSO$_4$ and recording the increase in 270-nm absorbance of Mn(III)-malonic acid complex generated by the reaction over time. In the case of pLC1MC, the Mn(III)-malonic acid complex was observed in the above supernatant at a level of enzyme activity of 5 μmol/ml/min 6 days after the start of culture. In the case of pLC2MP the complex was at 4 μmol/ml/min. Here, one unit of the enzyme activity is defined as an activity increasing 1 μmol of the Mn(III)-malonic acid complex over 1 minute. On the other hand, this activity was not recognized in the supernatant of the target DNA-free strain OJI-1078 cultured under the same conditions.

Figure 3:
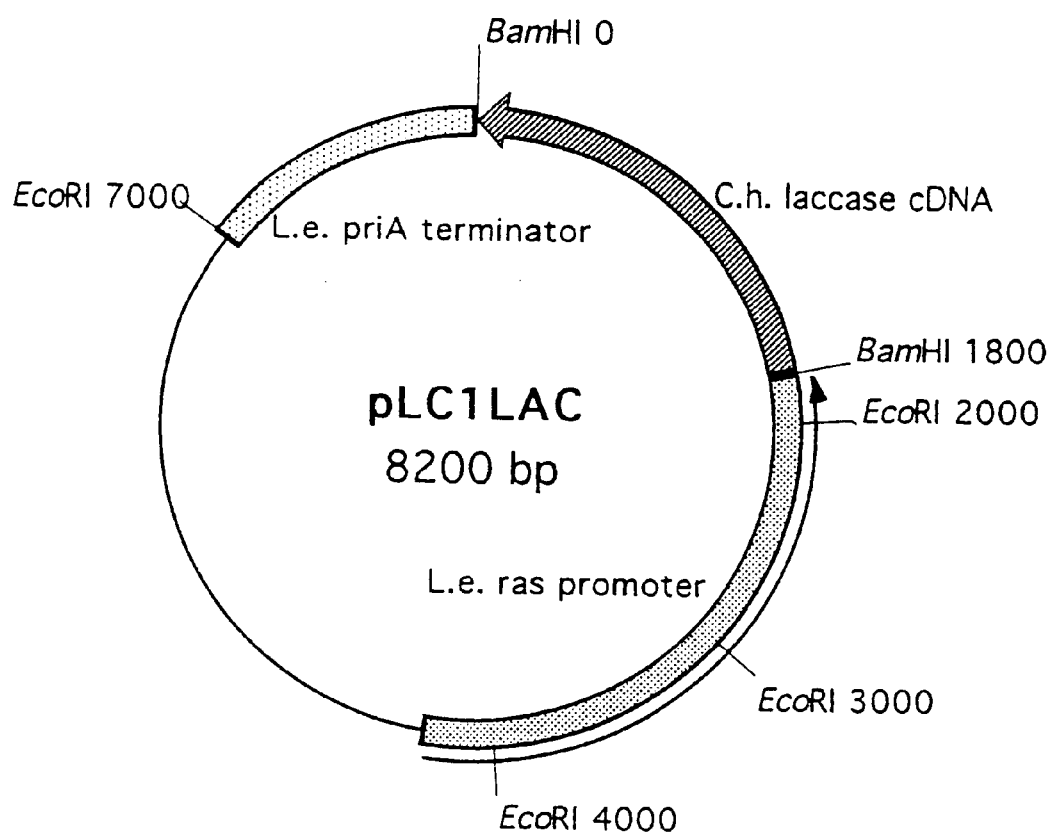
FIG. 3 shows a plasmid pLC1LAC containing a Coriolus hirsutus-derived laccase gene whose expression regulation is governed by a Lentinus edodes ras gene promoter region.

Example 6
Construction of Expression Vector Containing Coriolus hirsutus-Derived Laccase Gene with Lentinus edodes-Derived ras Gene Promoter A plasmid pLC1 (6.4 kb) containing a Lentinus edodes-derived ras gene promoter region (2.5 kb) and a priA gene terminator region (1.2 kb) was digested with a restriction enzyme BamHI (Takara Shuzo Co., Ltd., Kyoto, Japan), followed by ligating a Coriolus hirsutus-derived laccase cDNA gene (Accession No. FERM P-10055) to the BamHI site in the forward direction to prepare a laccase gene expression vector, which was designated as pLC1LAC (FIG. 3).

Figure 4:
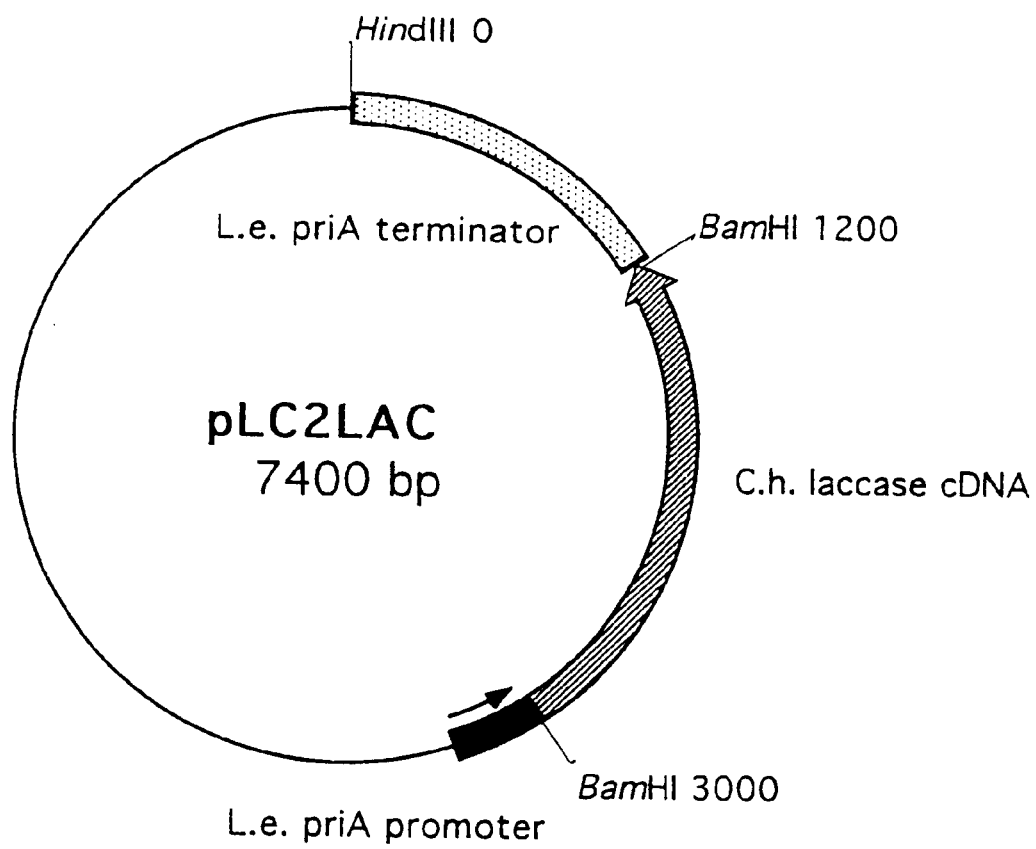
FIG. 4 shows a plasmid pLC2LAC containing a Coriolus hirsutus-derived laccase gene whose expression regulation is governed by a Lentinus edodes priA gene promoter region.

Example 7
Construction of Expression Vector containing Coriolus hirsutus-Derived Laccase Gene with Lentinus edodes-Derived priA Gene Promoter A plasmid pLC2 (5.6 kb) containing a Lentinus edodes-derived priA gene promoter region (0.4 kb) and a priA gene terminator region (1.2 kb) was digested with a restriction enzyme BamHI (Takara Shuzo Co., Ltd., Kyoto, Japan), followed by ligating Coriolus hirsutus-derived laccase cDNA gene (Accession No. FERM P-10055) to the BamHI site in the forward direction to prepare a laccase gene expression vector, which was designated as pLC2LAC (FIG. 4).

Example 8
Culture of Highly Laccase-Producible Strain

Each of the laccase gene expression vectors obtained in Examples 6 and 7 according to the method described in Example 3 was introduced into a host cell of Coriolus hirsutus strain 1078. Five 50-mm$^2$ agar pieces of each transformant was inoculated into 50 ml of a glucose-peptone liquid medium (30 g/l glucose, 10 g/l peptone, 1.5 g/l KH$_2$PO$_4$, 0.5 g/l MgSO$_4$·7H$_2$O, 100 mg/l CuSO$_4$·5H$_2$O; adjusted to pH 5.0 with phosphoric acid) in a 500-mL conical flask and cultured at 28° C. for 6 days with shaking. Six days later, the obtained culture was centrifuged to obtain the supernatant.

The enzyme activity was measured by mixing 50 μl of 1 M sodium acetate buffer (pH 4.0), 50 μl of 5 mM 2,2'-azino-bis(3-ethilbenzthiazoline-6-sulfonate) (ABTS)and 400 μl of enzyme solution and recording the increase in 420-nm absorbance of ABTS oxide generated by the reaction over time. In the case of pLC1LAC, the enzyme activity in the above supernatant was 34 units/ml on the 5th day after the start of culture. In the case of pLC2LAC, it was 26 units/ml. Here, one unit of the enzyme activity is defined as the quantity of enzyme requiring to oxidize 1 μmol of ABTS over 1 minute. On the other hand, the activity recognized in the supernatant of the target DNA-free strain OJI-1078 cultured under the same conditions was only 5 units/ml.

Example 9
Preparation of Chromosomal Gene Library

Agar piece (5 mm diameter) was punched out from a plate agar culture of Coriolus hirsutus (IFO4917 strain available from the IFO, Osaka, Japan) using a cork borer, inoculated into 200 ml of a glucose-peptone liquid medium (2% glucose, 0.5% polypeptone, 0.2% yeast extract, 0.1% KH$_2$PO$_4$, 0.05% MgSO$_4$·7H$_2$O; adjusted to pH 4.5 with phosphoric acid), and subjected to rotary shaking culture at 28° C. for 7 days. Then, the cell culture was harvested, washed with 1 liter of sterile water and then frozen with liquid nitrogen. Five g of this frozen cells were pulverized using a motor. After transferring the pulverized cells to a centrifugal tube, 10 ml of a bacterium-lysis buffer (100 mM tris (pH 8), 100 mM EDTA, 100 mM NaCl; further supplemented with Proteinase K at a concentration of 100 μg/ml) was added and the mixture was incubated at 55° C. for 3 hours. The incubated mixture was treated with phenol and then with chloroform. Subsequently, ethanol was gradually added to the aqueous phase until DNA was separated out, and the separated chromosomal DNA was wound up and suspended in a TE solution.

100 μg of the obtained chromosomal DNA was partially digested with a restriction enzyme Sau3AI, and fractionated by 5% to 20% sucrose gradient centrifugation (30,000 rpm, 18 hours) to pool 20–40 kbp fragments. These fragments were ligated to phage λ EMBL3 -BamHI arm (Toyobo, Co., Ltd., Kyoto, Japan) with T4DNA ligase. After packaging the obtained phage DNA using a GIGAPACK GOLD (STRATAGENE, USA), it was infected with Escherichia coli strain P2392 to prepare a chromosomal DNA library.

Example 10
Isolation of ras Gene from Chromosomal Gene Library

The selection of a clone containing an ornithine carbamoyl-transferase gene from the above chromosomal DNA library was carried out by plaque hybridization. This series of procedures were carried out according to ordinary methods such as those described in Sambrook et al., "Molecular Cloning" A Laboratory Manual/2nd Edition (1989).

The probe used in the plaque hybridization was prepared by radiolabeling synthetic oligomers having the following sequence with $^{32}$P:

SEQ ID NO:4:
5'-CA(T/C)TT(T/C)GIGA(T/C)GA(A/G)TA(T/C)GA-3'

As a result, 4 positive clones could be selected from approximately 40,000 plaques. Recombinant phage DNAs prepared from the positive clones according to an ordinary method were digested with various restriction enzymes, and Southern Hybridization was carried out using the above synthetic DNAs. As a result, a clone hybridizing to a single 3.5 kbp DNA band was found in fragments obtained by digestion with a restriction enzyme BamHI.

A 3.5-kbp DNA fragment was cut out of a gel following agarose gel electrophoresis, subcloned into the BamHI site of Escherichia coli vector pUC19, and transformed into Escherichia coli strain JM109. The subcloned DNA was prepared in a large quantity, purified by centrifugation (50,000 rpm, 16 hrs, 15° C.) and determined for its nucleotide sequence. The sequencing was carried out using a sequenase kit (United States Biochemical, Inc., USA).

The nucleotide sequence is given in SEQ ID NO:2. As seen in this sequence, the Coriolus hirsutus-derived ras gene is discontinued by 6 introns in the above nucleotide sequence. Furthermore, the amino acid sequence deduced from the nucleotide sequence was found to have a high homology to those of ras genes which had previously been reported. The amino acid sequence is given in SEQ ID NO:3.

The obtained Escherichia coli strain E. coli DH5α/ pCHRAS containing Coriolus hirsutus ras gene was deposited under the terms of the Budapest Treaty at the National Institute of Bioscience & Human-Technology, Agency of Industrial Science & Technology (Higashi 1-1-3, Tsukuba-shi, Ibaraki-ken, Japan) with Accession No. FERM BP-7001 (which was the one transferred to the international deposit on Jan. 20, 2000 from FERM P-17352 deposited on Mar. 30, 1999).

Example 11
Ligation of OCT Structural Gene Governed by ras Gene Control Region

A selective marker plasmid pCHRPRG for the expression of OCT of a basidiomycete Coriolus hirsutus was a selective marker prepared by ligating the structural gene region of the OCT chromosomal gene (Japanese Patent Application Laid-open No. 054691/1994; FERM BP-4201) to a site downstream of ras gene promoter region thereby to substitute the ras gene promoter region for the promoter region of the native OCT gene.

From a plasmid pCHRAS containing Coriolus hirsutus-derived ras gene promoter region, a DNA fragment containing the Coriolus hirsutus-derived ras gene promoter region was amplified by PCR method using the following 2 primers:

Primer-1: 5'-GGATCCCGCTATACCGAAAGG-3' (SEQ ID NO:5)
Primer-2: 5'-CCATGGCTGTATGGCGGAGG-3' (SEQ ID NO:6)

to give a 1.4 kbp BamHI-NcoI fragment which was then ligated to a unique SmaI site of pUC18 using T4 DNA ligase to obtain a plasmid pCHRP.

On the other hand, in order to isolate a gene region encoding a matured enzyme of OCT, the plasmid pUCR1 (Japanese Patent Application Laid-open No. 054691/1994; FERM BP-4201) was digested with a restriction enzyme NcoI to obtain approximately 2.5-kbp DNA fragment.

Figure 6:
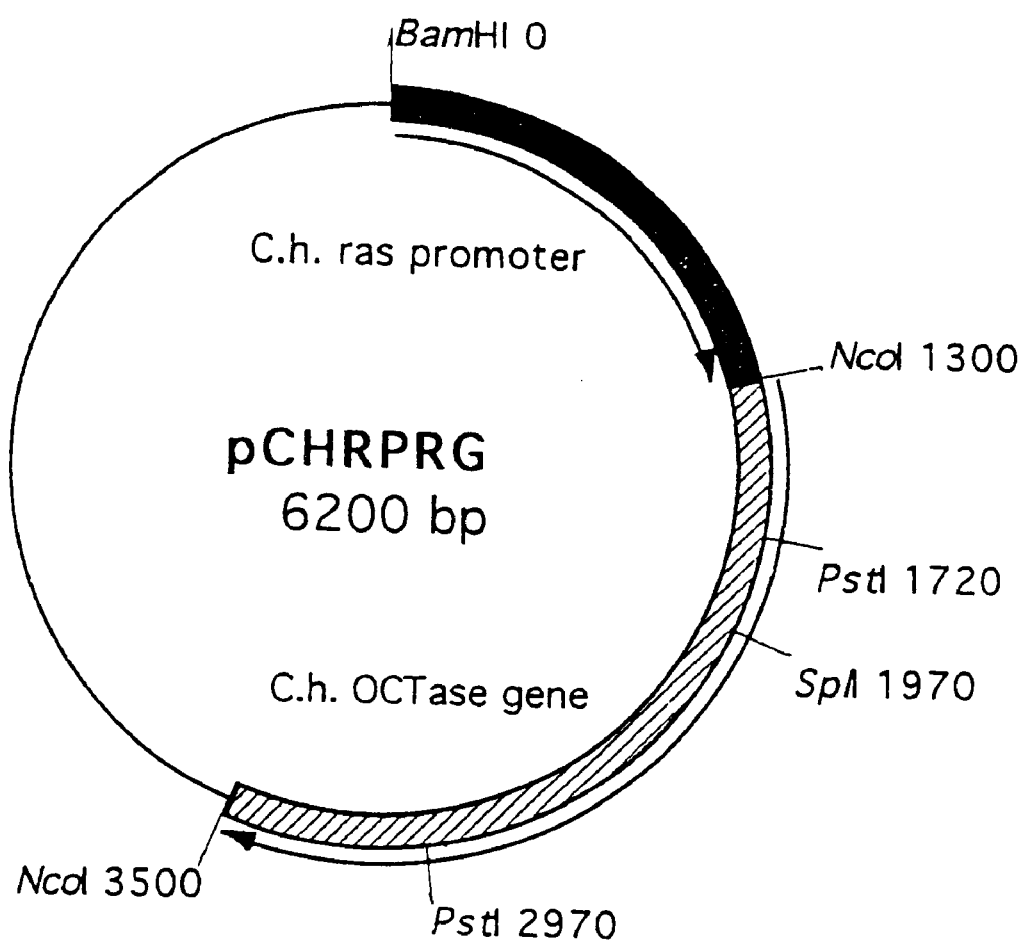
FIG. 6 shows the structure of the plasmid pCHRPRG for use in transformation of an arginine-requiring Coriolus hirsutus mutant illustrated in Example 11 below.

The foregoing 2 kinds of DNA fragments were mixed, ligated together using T4DNA ligase, and transformed into Escherichia coli strain JM109. A plasmid into which the OCT gene had been inserted in the forward direction was isolated from the ampicillin-resistant transformant strains and was designated as pCHRPRG (FIG. 6).

Example 12
Transformation of Coriolus hirsutus

To 100 μl of a protoplast suspension having a concentration of $10^6$/100 μl obtained in the same manner as in (a) to (c) of Example 3, 2 μg of the plasmid pCHRPRG prepared in Example 11 was added and ice-cooled for 30 minutes. Then, an equal volume of a PEG solution (50% PEG3400, 20 mM MES (pH 6.4)) was added to the above solution, followed by ice-cooling for 30 minutes. Next, the ice-cooled mixture was mixed with a minimum soft agar medium (1% agar) containing 0.5 M sucrose and leucine and inoculated onto a plate. The plate was cultured at 28° C. for several days to obtain transformants. The transformation efficiency was 300 colonies/μg of transformed DNA. In contrast, in the control experiment using a DNA consisting of the plasmid vector pUC18 alone, any transformant was not obtained at all.

Example 13
Construction of Expression Vector Containing Coriolus hirsutus-Derived Manganese Peroxidase Gene with Coriolus hirsutus-Derived ras Gene Promoter From a plasmid pCHRAS containing a Coriolus hirsutus-derived ras gene promoter region, the promoter region was amplified by PCR method using the following 2 primers:
Primer-1: 5'-GGATCCCGCTATACCGAAAG-3' (SEQ ID NO:5)
Primer-2: 5'-CCATGGCTGTATGGCGGAGG-3' (SEQ ID NO:6)
to give a 1.4 kbp BamHI-NcoI fragment which was then ligated to a unique SmaI site of pUC18 with T4DNA ligase to obtain a plasmid pCHRP.

The obtained plasmid pCHRP was digested with restriction enzymes NcoI and EcoRI (Takara Shuzo Co., Ltd., Kyoto, Japan) and then served as an expression vector.

Figure 7:
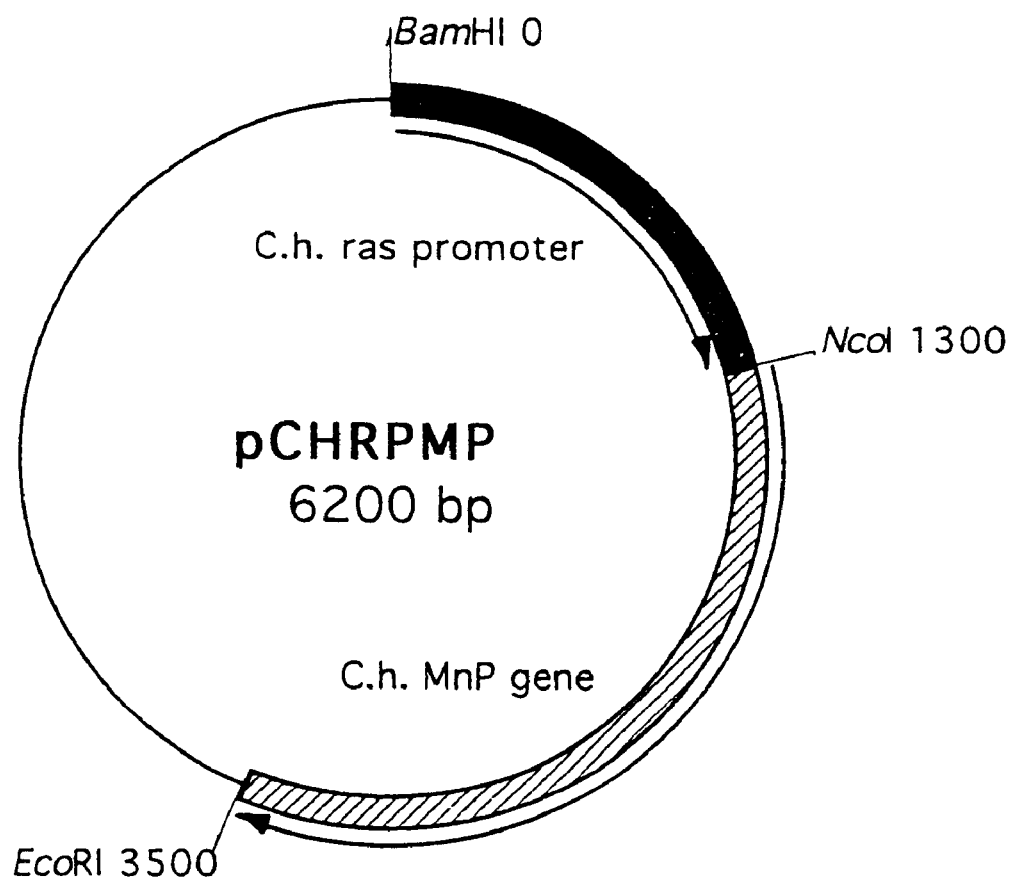
FIG. 7 shows the structure of the manganese peroxidase-expressing vector pCHRPMP illustrated in Example 13 below.

Next, an approximately 2.2 kb NcoI-EcoI fragment, which was a manganese peroxidase structural gene portion of a plasmid pBSMPOG1 (Accession No. FERM P-14933) containing a Coriolus hirsutus-derived manganese peroxidase gene, was amplified by PCR method using the following 2 primers:
Primer-1: 5'-CCATGGCTTTCAAGACACTCG-3' (SEQ ID NO:7)
Primer-2: 5'-GAATTCGCATGTAGGTCCGCG-3' (SEQ ID NO:8)
The obtained PCR fragment was inserted into the plasmid using TA cloning kit (In Vitrogen, Inc.) to prepare pTAMP. Then, the obtained pTAMP was digested with restriction enzymes NcoI and EcoRI to obtain approximately 2.2 kb fragment which was inserted into the NcoI-EcoRI sites of the pCHRP to obtain a plasmid pCHRPMP (FIG. 7).

Example 14
Preparation of Coriolus hirsutus Transformant Highly Secreting and Producing Manganese Peroxidase In transforming an arginine-requiring Coriolus hirsutus (OJI-1078 strain) with the pCHRPMP obtained in Example 13, a transformant pCHRPMP/OJI-1078 was obtained by simultaneously introducing a Coriolus hirsutus-derived OCT gene-carrying plasmid (pUCR1) as a selective marker (according to PEG method, electroporation or the like). Here, whether a DNA which can be subjected to transformation is in a circular or linear form, this transformation method could provide a transformant of interest. The conditions of transformation are as follows.

Two μg of the plasmid prepared in Example 13 was added to 100 μl of the protoplast suspension having a concentration of approximately $10^6$ cells/100 μl in a circular or linear form, followed by addition of 0.2 μg of pUCR1 as a selective marker then 30-minute ice-cooling.

Next, an equal volume of a PEG solution (50% PEG3400, 20 mM MES (pH 6.4)) was added and the mixture was ice-cooled for 30 min. The ice-cooled mixture was mixed with a minimum soft agar medium (1% agar) containing 0.5 M sucrose and leucine and inoculated onto a plate. The plate was cultured at 28° C. for 4 days, whereby a transformant was obtained. From this transformed strain, a DNA is prepared, which was subjected to Southern hybridization in order to confirm that the manganese peroxidase-expressing plasmid of interest had been introduced into the strain.

Example 15
Production of Manganese Peroxidase by Transformant

Five 50-mm$^2$ agar pieces containing the transformant strain obtained in Example 14 were inoculated into 50 ml of a glucose-peptone liquid medium (30 g/l glucose, 10 g/l peptone, 1.5 g/l $KH_2PO_4$, 0.5 g/l $MgSO_4·7H_2O$, 2 mg/l thiamine HCl, 48 mg/l $MnSO_4·5H_2O$; adjusted to pH 5.0 with phosphoric acid) in a 500-mL conical flask and cultured at 28° C. for 6 days with shaking. After 6 days, the obtained culture solution was centrifuged to obtain the supernatant.

The enzyme activity was measured by well mixing 50 μl of 0.5 M sodium malonate buffer (pH 5.5), 345 μl of enzyme solution, 5 μl of 10 mM hydrogen peroxide and 100 μl of 1 mM $MnSO_4$ and recording the increase in 270-nm absorbance of Mn(III)-malonic acid complex generated by the reaction over time. In the above supernatant, the Mn(III)-malonic acid complex was observed at a level of enzyme activity of 6 μmol/ml/min 6 days after the start of culture. Here, one unit of the enzyme activity is defined as an activity increasing 1 μmol of the Mn(III)-malonic acid complex over 1 minute. On the other hand, this activity was not observed in the supernatant of the target DNA-free strain OJI-1078 cultured under the same conditions.

Example 16
Construction of Expression Vector Containing Coriolus hirsutus-Derived Laccase Gene with Coriolus hirsutus-Derived ras Gene Promoter The plasmid pCHRPMP obtained in Example 13 was digested with a restriction enzyme NcoI (Takara Shuzo Co., Ltd., Kyoto, Japan), blunt-ended with Klenow fragment, and digested with a restriction enzyme EcoRI to prepare the expression vector portion.

Next, a plasmid OJ-POG-E1 (Accession No. FERM BP-2793) containing a Coriolus hirsutus-derived laccase gene was amplified by PCR method using the following 2 primers:

Primer-1: 5'-CTCGAGGTTCCAGTCTCTG-3' (SEQ ID NO:9)
Primer-2: 5'-GAATTCCCGGGGACGTATACG-3' (SEQ ID NO:10)

The resulting PCR fragment was introduced into the TA-cloning vector to obtain pTALAC.

Figure 8:
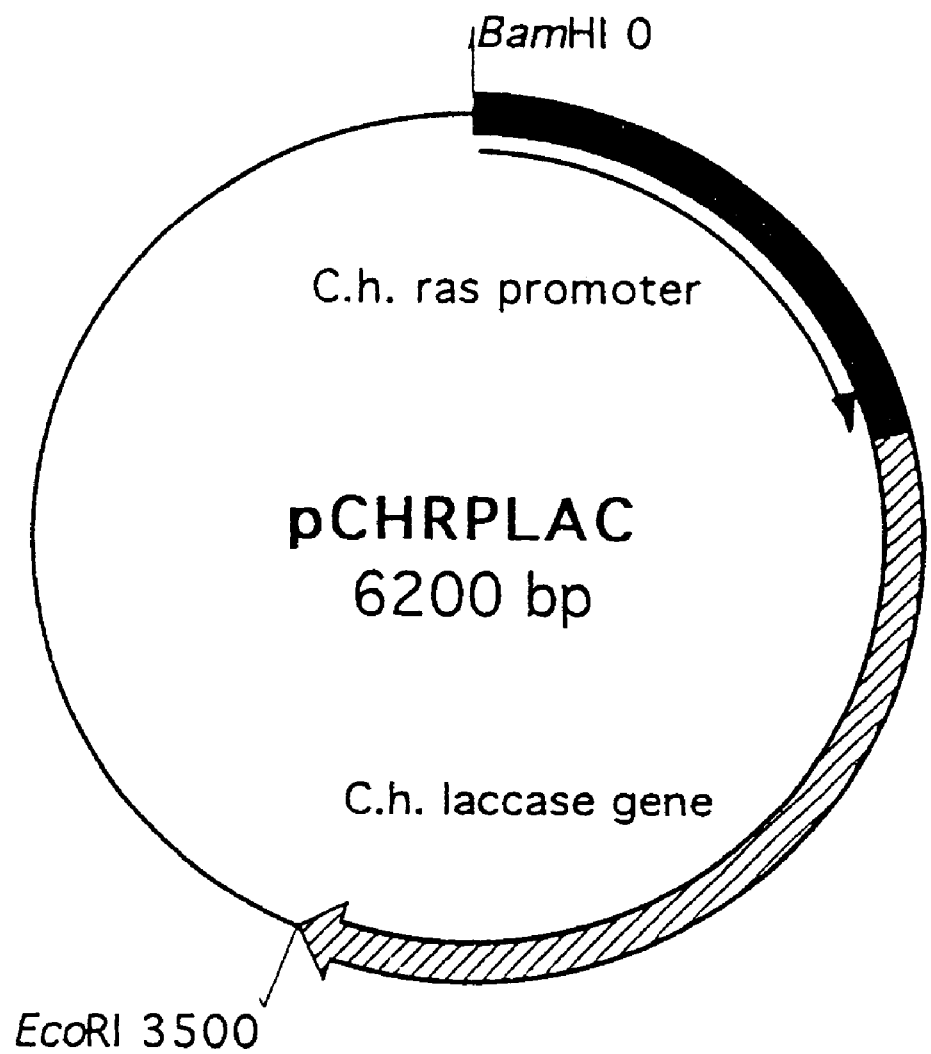
FIG. 8 shows the structure of the laccase-expressing vector pCHRPLAC illustrated in Example 16 below.

The obtained pTALAC was digested with restriction enzyme XhoI, blunt-ended with an modification enzyme Klenow fragment, digested with a restriction enzyme EcoRI to obtain the laccase structural gene portion, which was then introduced into the ras expression vector pCHRP treated above. The obtained plasmid was designated as pCHRPLAC (FIG. 8).

Example 17
Preparation of Coriolus hirsutus Transformant Highly Secreting and Producing Laccase In transforming an arginine-requiring Coriolus hirsutus (OJI-1078 strain) with pCHRPLAC obtained in Example 16, a transformant pCHRPLAC/OJI-1078 was obtained by simultaneously introducing a Coriolus hirsutus OCT gene-carrying plasmid (pUCR1) as a selective marker (according to PEG method, electroporation or the like). Here, whether a DNA which can be subjected to transformation is in a circular or linear form, this transformation method could provide the transformant of interest. The conditions of transformation are as follows.

Two μg of the plasmid prepared in Example 8 was added to 100 μl of the protoplast suspension having a concentration of approximately $10^6$ cells/100 μl in a circular or linear form, followed by addition of 0.2 μg of pUCR1 as a selective marker then 30-minute ice-cooling.

Next, an equal volume of a PEG solution (50% PEG3400, 20 mM MOPS (pH 6.4)) was added and the mixture was ice-cooled for 30 min. The ice-cooled mixture was mixed with a minimum soft agar medium (1% agar) containing 0.5 M sucrose and leucine and inoculated onto a plate. The plate was cultured at 28° C. for 4 days, whereby a transformant was obtained. From this transformant strain, a DNA is prepared, which was subjected to Southern hybridization in order to confirm that the target laccase-expressing plasmid had been introduced into the strain.

Example 18
Production of Laccase by Transformant

Five 50-mm$^2$ agar pieces containing the transformant strain obtained in Example 17 were inoculated into 50 ml of a glucose-peptone liquid medium (30 g/l glucose, 10 g/l peptone, 1.5 g/l $KH_2PO_4$, 0.5 g/l $MgSO_4·7H_2O$, 2 mg/l thiamine HCl, 100 mg/l $CuSO_4·5H_2O$; adjusted to pH5.0 with phosphoric acid) in a500-mL conical flask and cultured at 28° C. for 6 days with shaking. After 6 days, the obtained culture solution was centrifuged to obtain the supernatant.

The enzyme activity was measured by mixing 50 μl of 1 M sodium acetate buffer (pH 4.0), 50 μl of 5 mM 2,2'-azino-bis(3-ethilbenzthiazoline-6-sulfonate) (ABTS) and 400 μl of enzyme solution and recording the increase in 420-nm absorbance of ABTS oxide generated by the reaction over time. In the above supernatant, the enzyme activity was 40 units/ml on the 5th day after the start of culture. Here, one unit of the enzyme activity is defined as the quantity of an enzyme requiring to oxidize 1 μmol of ABTS over 1 minute. On the other hand, the activity observed in the supernatant of the target DNA-free strain OJI-1078 cultured under the same conditions was only 5 units/ml.

INDUSTRIAL APPLICABILITY

The present invention provides a novel promoter region which functions in Coriolus hirsutus and enables the production of a lignin degrading enzyme, the mass production of the enzyme by genetic recombination having been considered to be difficult. Particularly, the transformant Coriolus hirsutus having an ability to highly degrade lignin according to the present inven-tion has a property of acting on lignin so as to degrade it into low-molecular-weight products, so it can be applied to various steps in paper and pulp production processes using a lignocellulose material (e.g., wood) as a raw material, that is, steps such as pulping, pulp bleaching, and waste water treatment. Moreover, in saccarification of wood, this transformant can also be applied to the field of a so-called cellulose biomass utilization for increasing the action of cellulase by degrading lignin in a treatment preceding the saccarification.

The respective sequences of SEQ ID NOS:1, 2 and 3 described herein are as follows:

```
SEQ ID NO:1:
ggatccgcta taccgaaagg ccgcgacgtc ctacacatgt cagtcaagag aacatgatgg      60
gcgtcatgtg gacagccgag ctgaggatgt attgcgcgag ggtgttcatc gagctgcgcg     120
tttccgagaa ctgctgtaga acggacgagg agcttcgaga ggggctgcga tggtgggaaa     180
tatctttccg gcggttttgg aagggccatt aagagcagag agatgcccgt ccaggacagg     240
gaaggtcggg tgcggactgt ggagcatccg cctgcgatcc tacatgagac cggggggcgag    300
acggacatct gggaaaggaa tgacatgcag ggaccgtgag aggatataca tgaatggtgg     360
tggtagacat accacgatgc tgggaacact atccgtgatg ttctcgcttg caccagaaag     420
gactgcaggt ggggagcaat cgcgccgaca ggtggcgtgc tatgcagaac cgcggcagtc     480
tcgacagcac cttacctctt ggacgtatca ctcacagtcc tctcggccct tcagatccaa     540
tcgatcccgt agtaacgtgc gtcatctagg agtggaaggt tggttgaccg acctgacaag     600
acataaccgg atgcccattc ggaaggctcg gggggccaag cgacctccgt gtatgatcgc     660
atgctatagc tcgacgtcgg gccgatagcg gcgcaaatca gagcaccgaa tgatgaagca     720
tctgagggaa gatcattgca tgagccatcc tgaacaggtt cgcaacgcgt ctgggaacga     780
gatgccatgc tgctacggtg atcctgatga agcacagccc gagatgcttg gtgctggacc     840
ccattggaag ctgctcgact tccttgtatg ataatcggtc tacatttctc gaccacagtt     900
gcgcatccgc ggtcagctga catcgaaggg gagcagtagt acagttggtg agctctcggg     960
ccttcgcggc gcattgccaa agacaccacc gaatattgcg aggccttgcg cagcgcgatg    1020
tggctaaata tgccagagca gctgtataag ggccctgtga ctcaccatgc gagaactgcg    1080
atatgtggct gtcagataat gcgatatacg agtcggagcg gaggcggaac tggggctggt    1140
agggactcta cttattgcgg taccggtcag aggatggcag cgttcagtga caagtcgcga    1200
agcgccgggc gcgagtattt ggctatgttt gcggcgcggt gtgttccaat agagggcgct    1260
tccacgtctt aattcccctg tcctcctcga cggatccacct ctcctccctc ccattcccgc   1320
ccttcaaata ccccccctcca cctcctcctc cgccatacag cc                      1362
SEQ ID NO:2:
ggatccgcta taccgaaagg ccgcgacgtc ctacacatgt cagtcaagag aacatgatgg      60
gcgtcatgtg gacagccgag ctgaggatgt attgcgcgag ggtgttcatc gagctgcgcg     120
tttccgagaa ctgctgtaga acggacgagg agcttcgaga ggggctgcga tggtgggaaa     180
tatctttccg gcggttttgg aagggccatt aagagcagag agatgcccgt ccaggacagg     240
gaaggtcggg tgcggactgt ggagcatccg cctgcgatcc tacatgagac cggggggcgag    300
acggacatct gggaaaggaa tgacatgcag ggaccgtgag aggatataca tgaatggtgg     360
tggtagacat accacgatgc tgggaacact atccgtgatg ttctcgcttg caccagaaag     420
gactgcaggt ggggagcaat cgcgccgaca ggtggcgtgc tatgcagaac cgcggcagtc     480
tcgacagcac cttacctctt ggacgtatca ctcacagtcc tctcggccct tcagatccaa     540
tcgatcccgt agtaacgtgc gtcatctagg agtggaaggt tggttgaccg acctgacaag     600
acataaccgg atgcccattc ggaaggctcg gggggccaag cgacctccgt gtatgatcgc     660
atgctatagc tcgacgtcgg gccgatagcg gcgcaaatca gagcaccgaa tgatgaagca     720
tctgagggaa gatcattgca tgagccatcc tgaacaggtt cgcaacgcgt ctgggaacga     780
```

```
                                                        -continued
gatgccatgc tgctacggtg atcctgatga agcacagccc gagatgcttg gtgctggacc      840
ccattggaag ctgctcgact tccttgtatg ataatcggtc tacatttctc gaccacagtt      900
gcgcatccgc ggtcagctga catcgaaggg gagcagtagt acagttggtg agctctcggg      960
ccttcgcggc gcattgccaa agacaccacc gaatattgcg aggccttgcg cagcgcgatg     1020
tggctaaata tgccagagca gctgtataag ggccctgtga ctcaccatgc gagaactgcg     1080
atatgtggct gtcagataat gcgatatacg agtcggagcg gaggcggaac tggggctggt     1140
agggactcta cttattgcgg taccggtcag aggatggcag cgttcagtga caagtcgcga     1200
agcgccgggc gcgagtattt ggctatgttt gcggcgcggt gtgttccaat agagggcgct     1260
tccacgtctt aattcccctg tcctcctcga cggatcacct ctcctccctc ccattcccgc     1320
ccttcaaata cccccctcca cctcctcctc cgccatacag ccatgtccag ggtgcgtaca     1380
ccgacacacg gcgctgtcag ctatcctgac gcctgcgcag tcccagttct tgcgcgagta     1440
caagcttgtc gtcgtcggcg gtggtggtca gttccccggc tcgctagcat cccggactcg     1500
tctcacgcgt cctttcaggt gtcggcaagt ccgcactcac tatccagttc atccagagtc     1560
acttcgtgga cgagtatgac cctaccatcg aaggtgtgta cctgttcctg acgctctcgc     1620
ccacgtcgtc tcccgcttgc gaccatgccg catggccgag acgtcttgcg ttcccgcgaa     1680
gctttcccat ggtacgcgtg ctcacggcac ctcttacaga ctcgtaccgt aagcaatgcg     1740
tgattgacga tgaggtcgcg ctcctcgacg tcttggatac cgctggccag gaggaatacg     1800
ggtgcgtcta tcctctacac tccgtttcct cgcctctcac aacgtttgtt tgcgccgtgc     1860
agtgcgatgc gtgagcagta catgcgcacg ggggagggct tcctgctggt ctactccatc     1920
acttcgcgca actcgttcga ggaaatcagc acgttccatc agcagatcct acgcgtaaag     1980
gaccaggact cgttcccggt catcgtcgtc gcaaacaagt gcgacttgga gtacgagcgg     2040
caggtgggaa tgaatggtac gttcacctcc ccacccttgc tcggtagact gcgtgtgctg     2100
actaagtgtg tgcgccgtgc agagggccgt gatctcgcga agcacttcgg ctgcaagttc     2160
atcgagactt cggcgaagaa ccgcatcaac gtcgacgagg cgttcagtca gctcgtccgc     2220
gagatccgga agtacaacaa ggttcgttcg ccacaatttg ccgttaccac aggctccagt     2280
acttacctct cccgcaggag caacaaaccg gacgtccggg cgtgcagccc agcgcaccta     2340
gcgcccctgg cgtgtacggc aacgaaaagg gacacccaga cgacggcgcg ggcggatgct     2400
gtggctgcgt tgtcgcgtaa ccgtcccatc cctcctccct tccttcatcg tttctttttcc     2460 atcggtttgg gctcttcctg cgtaccccgt tcttctcgtc ctgccacacc ctcatcgtcg     2520
ccattgcccg tcgtcactgc cagttctccc ccggatatca agatgtctct catctcccgc     2580
tgctgttctg tttttatgta ttccttactc ttctgcgctc gtctgtccgt ctgaacatca     2640
tacctcgtgc ctagttcgcg ccgttggtgt gcgttctctg tttgtgactg tcggcattta     2700
```

-continued

```
ctgtccctac tcgttcgtcc cgattgattg ctgctgttca ttggattgac ggccgaatca    2760
aacatataga ggctttgagc cagagtcaaa ttatgatttg actagactag tgagaaagca    2820
gatttcgaca ccaccccgtt cgttgatcaa ggactgagta tggcgatacc tggtatggat    2880
cagctcaagg attcttgtgc ttgttgtata cagcgccatg tcaagcactc agtttgttct    2940
cgcacgtgcc ttggcctggg tcattccgag aatccatcca ctgtcgcagg atctacgtct    3000
gccgccgcat gcatgccagt cccgaggcgg ctgaagtctg aggctctgag cagcccaact    3060
acagcctaac tgctggctag tacgtgagtc tgtcccaaga cattattcgc tctattacag    3120
cacactgacc ttcgctttga acagctcctt gcgactatat aggcaccgat gtgcctccgc    3180
cacagagcac tacactcagg aagccacgct gtcaaggaat gcgcacatga tagtccgaga    3240
agcgcatggc gctacgcgga atgggcacca agtgtccgcg tcaggtttgg tctggcattc    3300
ttctgatctt cccccgggct gaccgcaggt ggcccagatg cttgtttgtc ggcgctataa    3360
agtaggtgga cccgagtttc tcccagtctt tcgtaggtgg gcgactcgct acacagtcag    3420
aagagtacga catcctatgt agggctacaa cgactgccaa aacggaggct gtaagtgagg    3480
ctcacggatt cggatcc                                                   3497
```

SEQ ID NO:3:

```
Met Ser Arg Phe Leu Arg Glu Tyr Lys Leu Val Val Gly Gly Gly
 1               5                  10                  15

Gly Val Gly Lys Ser Ala Leu Thr Ile Gln Phe Ile Gln Ser His Phe
                20                  25                  30

Val Asp Glu Tyr Asp Pro Thr Ile Glu Asp Ser Tyr Arg Lys Gln Cys
             35                  40                  45

Val Ile Asp Asp Glu Val Ala Leu Leu Asp Val Leu Asp Thr Ala Gly
         50                  55                  60

Gln Glu Glu Tyr Gly Ala Met Arg Glu Gln Tyr Met Arg Thr Gly Glu
 65                  70                  75                  80

Gly Phe Leu Leu Val Tyr Ser Ile Thr Ser Arg Asn Ser Phe Glu Glu
                 85                  90                  95

Ile Ser Thr Phe His Gln Gln Ile Leu Arg Val Lys Asp Gln Asp Ser
             100                 105                 110

Phe Pro Val Ile Val Val Ala Asn Lys Cys Asp Leu Glu Tyr Glu Arg
         115                 120                 125

Gln Val Gly Met Asn Glu Gly Arg Asp Leu Ala Lys His Phe Gly Cys
     130                 135                 140

Lys Phe Ile Glu Thr Ser Ala Lys Asn Arg Ile Asn Val Asp Glu Ala
145                 150                 155                 160

Phe Ser Gln Leu Val Arg Glu Ile Arg Lys Tyr Asn Lys Glu Gln Gln
                165                 170                 175

Thr Gly Arg Pro Gly Val Gln Pro Ser Ala Pro Ser Ala Pro Gly Val
            180                 185                 190

Tyr Gly Asn Glu Lys Gly His Pro Asp Asp Gly Ala Gly Gly Cys Cys
        195                 200                 205

Gly Cys Val Val Ala
    210
```

Those skilled in the art will construe that various variations and modifications are possible within the scope of the invention described in the attached claims and the scope of its equivalence referring to the above descriptions. It therefore should be understood that the present invention includes such variations and modifications too.

In addition, it is contemplated that all the publications and patent applications cited above, as well as two priority applications claimed in the present application, are incorporated herein by reference in their entireties.

What is claimed is:

1. A Coriolus hirsutus host cell transformed with a vector containing a promoter region selected from the group consisting of a ras gene promoter region derived from Coriolus hirsutus, a ras promoter region derived from Lentinus edodes, and a priA gene promoter region derived from Lentinus edodes.

2. A Coriolus hirsutus host cell according to claim 1, wherein the vector further comprises a gene encoding a useful polypeptide is transcribably ligated at a site downstream of said promoter gene.

3. A Coriolus hirsutus host cell according to claim 2, wherein said gene encoding a useful polypeptide is a gene coding for a lignin degrading enzyme such as manganese peroxidase, lignin peroxidase, or laccase gene.

4. A process for producing a useful polypeptide comprising culturing the Coriolus hirsutus host cell defined in claim 1 in a medium and recovering the formed useful polypeptide.

5. A process according to claim 4, wherein the useful polypeptide is a lignin degrading enzyme such as manganese peroxidase, lignin peroxidase, or laccase.

6. An isolated DNA fragment containing a Coriolus hirsutus-derived ras gene promoter region as shown in SEQ ID NO: 1.

7. An isolated DNA fragment according to claim 6, wherein the DNA fragment has a nucleotide sequence shown in SEQ ID NO:1 or a sequence that hybridizes to a sequence complementary to the said nucleotide sequence under stringent conditions and has a promoter activity.

8. A recombinant DNA containing a gene encoding a useful polypeptide and the DNA fragment defined in claim 6, the gene being transcribably linked to the DNA fragment.

9. A recombinant DNA according to claim 8, wherein the gene encoding a useful polypeptide is a gene coding for a lignin degrading enzyme such as manganese peroxidase, lignin peroxidase, or laccase.

10. An isolated DNA which contains a Coriolus hirsutus-derived ras gene promoter sequence and a ras gene sequence and has a nucleotide sequence shown in SEC ID NO: 2.

11. A vector containing the DNA fragment defined in claim 8 or the recombinant DNA defined in claim 8.

12. A host cell transformed with the vector defined in claim 11.

13. A host cell according to claim 12, wherein the host is a basidiomycete.

14. A host cell according to claim 13, wherein the basidiomycete is Coriolus hirsutus.

15. A process for producing a useful polypeptide comprising culturing the host cell defined in claim 11 in a medium and recovering the formed useful polypeptide.

16. A process according to claim 15, wherein the useful polypeptide is a lignin degrading enzyme such as manganese peroxidase, lignin peroxidase, or laccase.

* * * * *

UNITED STATES PATENT AND TRADEMARK OFFICE
CERTIFICATE OF CORRECTION

PATENT NO.   : 6,387,688 B1
DATED        : May 14, 2002
INVENTOR(S)  : Kazuo Shishido et al.

It is certified that error appears in the above-identified patent and that said Letters Patent is hereby corrected as shown below:

Title page,
Item [57], ABSTRACT,
Line 2, "basidiomycete-derived" should read -- Basidiomycete-derived --.
Line 4, "basidiomycete-derived" should read -- Basidiomycete-derived --.
Line 6, "basidiomycete-derived" should read -- Basidiomycete-derived --.

Column 33,
Line 10, "SEC ID" should read -- SEQ ID --.
Line 12, "claim 8 or" should read -- claim 6 or --.

Column 34,
Line 2, "basidiomycete" should read -- Basidiomycete --.
Lines 3 and 4, "basidiomycete" should read -- Basidiomycete --.

Signed and Sealed this

Twelfth Day of November, 2002

*Attest:*

*Attesting Officer*

JAMES E. ROGAN
*Director of the United States Patent and Trademark Office*